(12) United States Patent
Maguire et al.

(10) Patent No.: US 8,501,727 B2
(45) Date of Patent: Aug. 6, 2013

(54) SHORT ACTING BENZOTHIAZEPINE CALCIUM CHANNEL BLOCKERS AND USES THEREOF

(75) Inventors: Martin P. Maguire, Westmount (CA); Dominik Herbart, Blainville (CA); Harry J. Leighton, Rockport, ME (US)

(73) Assignee: Milestone Pharmaceuticals Inc., Montréal, Québec (CA)

( * ) Notice: Subject to any disclaimer, the term of this patent is extended or adjusted under 35 U.S.C. 154(b) by 146 days.

(21) Appl. No.: 13/059,776

(22) PCT Filed: Aug. 20, 2009

(86) PCT No.: PCT/US2009/054501
§ 371 (c)(1),
(2), (4) Date: Mar. 3, 2011

(87) PCT Pub. No.: WO2010/022259
PCT Pub. Date: Feb. 25, 2010

(65) Prior Publication Data
US 2011/0144087 A1    Jun. 16, 2011

Related U.S. Application Data

(60) Provisional application No. 61/189,747, filed on Aug. 22, 2008.

(51) Int. Cl.
*A61K 31/554* (2006.01)
*C07D 281/10* (2006.01)
*A61P 9/10* (2006.01)
*A61P 9/12* (2006.01)
*A61P 7/00* (2006.01)

(52) U.S. Cl.
USPC ..................... 514/211.07; 540/491

(58) Field of Classification Search
None
See application file for complete search history.

(56) References Cited

U.S. PATENT DOCUMENTS

| | | | |
|---|---|---|---|
| 4,694,002 A | 9/1987 | Floyd et al. | |
| 4,946,840 A * | 8/1990 | Barrish et al. | ........... 514/211.07 |
| 5,002,942 A | 3/1991 | Yanagisawa et al. | |
| 5,336,774 A | 8/1994 | Achiwa | |
| 6,174,917 B1 | 1/2001 | McLean | |
| 6,750,238 B1 | 6/2004 | Erhardt | |
| 6,951,860 B2 | 10/2005 | Mehanna et al. | |
| 7,164,027 B2 | 1/2007 | Erhardt | |

FOREIGN PATENT DOCUMENTS

WO    WO 2006/079077 A2    7/2006

OTHER PUBLICATIONS

Inoue et al. "Synthesis and Biological Evaluation of Alkyl, Alkoxy, Alkylthio, or Amino-Substituted 2,3-Dihydro-1,5-benzothiazepin-4(5H)-ones", Chem. Pharm. Bull. 45 (6) 1008-1026 (1997). (compound 18u at table 7, p. 1021).*
Poon et al., Analogues of erectile dysfunction drugs: an under-recognised threat, Hong Kong Med. J., vol. 13, No. 5, Oct. 2007, p. 359.*
Wermuth, Similarity in Drugs: reflections on analogue design, Drug Discovery Today, vol. 11, No. 7/8, Apr. 2006, p. 349.*
Hagiwara et al., "High-affinity binding of DTZ323, a novel derivative of Diltiazem, to rabbit skeletal muscle L-type $Ca^{++}$ channels," *J. Pharmacol. Exp. Ther*. 281:173-179 (1997).
Inoue et al., "Synthesis of Halogen-substituted 1,5-Benzothiazepine derivatives and their vasodilating and hypotensive activities," *J. Med. Chem*. 34:675-687 (1991).
Yamada et al., "Optical resolution of a 1,5-Benzothiazepine derivative, a synthetic intermediate of Diltiazem, by preferential crystallization and diastereomeric salt formation," *Chem. Pharm. Bull*. 45:1922-1927 (1997).
International Preliminary Report on Patentability for PCT/US2009/054501, issued Feb. 22, 2011 (6 pages).
International Search Report for PCT/US2009/054501, mailed Oct. 2, 2009 (2 pages).
Written Opinion of the International Searching Authority for PCT/US2009/054501, mailed Oct. 2, 2009 (5 pages).

* cited by examiner

*Primary Examiner* — Ernst Arnold
*Assistant Examiner* — Jianfeng Song
(74) *Attorney, Agent, or Firm* — Clark & Elbing LLP

(57) ABSTRACT

The present invention relates to short-acting calcium channel blocking compounds and their use to treat ischemic heart conditions, cardiac arrhythmias, hypertensive crisis in an emergency room setting, hypertension in general, hypertension been.) fore, during, or after surgery, no-reflow phenomenon following reperfusion, and diseases associated with decreased skeletal muscle blood flow. The invention also relates to pharmaceutical compositions formulated for use in such methods and to kits for such methods.

28 Claims, No Drawings

SHORT ACTING BENZOTHIAZEPINE CALCIUM CHANNEL BLOCKERS AND USES THEREOF

CROSS-REFERENCE TO RELATED APPLICATIONS

This application is the U.S. National Stage filing under 35 U.S.C. §371 of International Application No. PCT/US2009/054501, filed Aug. 20, 2009, which claims the benefit of U.S. Provisional Patent Application No. 61/189,747, filed Aug. 22, 2008.

FIELD OF THE INVENTION

The invention relates to the use of benzothiazepine compounds which block L-type calcium channels to treat cardiovascular disorders.

BACKGROUND OF THE INVENTION

Calcium Channel Blockers

Calcium channel blockers (CCBs) are a chemically diverse class of compounds having important therapeutic value in the control of a variety of diseases including several cardiovascular disorders, such as hypertension, angina, and cardiac arrhythmias and include a heterogeneous group of drugs that prevent or slow the entry of calcium into cells by regulating cellular calcium channels. Calcium influx through these channels initiates a process of electromechanical coupling that ultimately leads to muscle contraction. The ability to regulate the entry of calcium into cardiac and vascular smooth muscle cells is a powerful therapeutic approach to the treatment of angina and hypertension, respectively. Likewise, blocking calcium influx into cardiac tissues and conduction systems provides a useful approach to control certain types of arrhythmia. Most of the currently available calcium channel blockers belong to one of three major chemical groups of drugs: the dihydropyridines, such as nifedipine, the phenylalkylamines, such as verapamil, and the benzothiazepines, such as diltiazem.

Serum Esterases

Serum esterases play an important role in the hydrolytic biotransformation of a vast number of structurally diverse drugs. These enzymes are major determinants of the pharmacokinetic behavior of most therapeutic agents containing ester bonds. Serum esterases are classified into three groups, A- B- and C-esterases, based on their interaction with organophosphates (De Vriese et al., *Endocrinology* (2004) 145, No. 11, 4997-5005). A-esterases, including arylesterase/paraoxonase, rapidly hydrolyze organophosphates. B-esterases, including acetylcholinesterase, butyrylcholinesterase, and nonspecific carboxylesterase, are inhibited by organophosphates. C-esterases, such as acetylesterase, do not interact with organophosphates.

Angina

Angina is a symptom of insufficient blood oxygen supply to an area of the heart due to an imbalance of the oxygen supply-demand ratio. Angina is usually precipitated following exertion, or emotional stress in susceptible patients due to an inability of the coronary vasculature to provide sufficient cardiac oxygen perfusion. A narrowing of the coronary arteries is often an underlying cause as a result of arteriosclerosis or vasospastic narrowing of blood vessels. Angina usually lasts less than 15 minutes and is typically treated by sublingual administration of nitroglycerin to relieve symptoms. Nitroglycerin and other nitrates induce vasodilation through release of nitric oxide (NO) thereby causing a lowering of blood pressure.

Angina can he classified as stable angina whose principal underlying cause is arteriosclerosis, vasospastic angina (also called variant angina or Prinzmetal angina) whose underlying cause is due to transient vasospasm of the coronary arteries, or unstable angina caused by platelet clotting at sites of ruptured arteriosclerotic plaques. Stable angina usually occurs as a result of exertion or stress whereas vasospastic angina can also be felt during periods of rest or in the early morning hours. Unstable angina is felt even during periods of rest and can signal imminent myocardial infarction. Sustained reduced blood flow (ischemia) to the heart can cause permanent damage to the heart due to the death of cardiac muscle. When coronary arteries are severely narrowed by more than 50-70%, the blood vessels can no longer supply the oxygen demands of the heart and angina is felt symptomatically as chest pain.

Cardiac Arrhythmia and Atrial Fibrillation

Arrhythmia, or abnormal heart rhythms, is caused by abnormal excitation and conduction to the heart. The mechanism of the onset of arrhythmia is categorized into three groups: (1) abnormal excitation, (2) abnormal conduction of excitation, and (3) a combination of abnormal excitation and abnormal conduction of excitation.

Atrial fibrillation is arrhythmia arising from abnormalities in the intrinsic pacemaker conductive potential of the heart. In atrial fibrillation, the electrical discharges are rapid and irregular, resulting in an irregular rhythm of heart contraction. In a normal heart, electrical discharges are generated in the sino-atrial node. In atrial fibrillation, electrical discharges are not generated exclusively in the sino-atrial node and come from other parts of the atria. These rapid and irregular discharges result in rapid and ineffectual atrial contractions that reduce the ability of the atria to supply blood to the ventricles.

A recurrent arrhythmia with an abrupt onset and termination is designated as paroxysmal. Paroxysmal supraventricular tachycardia (PSVT) presents as episodes of regular and paroxysmal palpitations with sudden onset and termination (Blomstrom-Lundqvist et al., 2003, *J Am Coll Cardiol*, 42:1493-531).

Atrial flutter is characterized by acute symptoms of palpitations, dyspnea, fatigue, or chest pain. In most instances, patients with atrial flutter have a two-to-one atrio-ventricular node (AV) conduction pattern. For example, the flutter rate of the atria can be 300 per minute with a ventricular rate of 150 beats per minute (Blomstrom-Lundqvist et al., 2003, *J Am Coll Cardiol*, 42:1493-531).

Blood Flow and Pressure Regulation

Hypertension is defined as high blood pressure, usually above 140 (systolic)/90 (diastolic). Hypertensive conditions can occur in relation to the conduction of surgical procedures. For example, blood pressure control is critical before, during, and after surgery. Hypertensive crisis arising from high blood pressure is subdivided into two categories: urgent and emergency. The symptoms of an emergency hypertensive crisis are more severe and may include brain swelling, stroke, pulmonary edema, heart attack or other symptoms. Both urgent and emergency categories hypertensive crisis involve a severe increase in blood pressure and require immediate treatment to prevent potential complications (i.e., stroke or damage to organs and tissues).

Raynaud's phenomenon is a disorder associated with restricted blood flow to body extremities such as the fingers, toes, ears and nose, and reflects an aberration of the normal response to cold involving peripheral vasoconstriction and restriction of blood flow to the extremities in order to protect the core body temperature. Attacks may be brought on by exposure to cold or emotional stress. Up to 5 to 10% of the population of the United States is affected, to some degree, by Raynaud's phenomenon.

Intermittent claudication is a condition that involves discomfort in the legs and occasionally the arms. It is due to a narrowing of the arteries and a resulting decrease in blood flow, particularly to muscles during physical exertion. The condition most commonly occurs in the calf muscle but may also affect the foot, hip or buttocks.

No-reflow phenomenon is a condition following reperfusion in which excessive or abnormal vasoconstriction occurs. The no-reflow phenomenon that occurs in about 2-5% of patients undergoing percutaneous transluminal coronary angioplasty (PTCA) is believed to be due to aggregation of platelets and neutrophils, which causes a blockage of blood flow within the vessels and vasoconstriction from substances released from the platelets. The condition is characterized by abnormal tissue perfusion. Persistent no-reflow is associated with higher clinical complication rates (Eeckhout, E. and Kern, M. J., *European Heart Journal* (2001) 22, 729-739).

Given the prevalence of cardiovascular disorders in patients, there is a need for new and improved compound and methods for treating cardiovascular disorders including ischemic heart conditions and cardiac arrhythmias.

SUMMARY OF THE INVENTION

The invention relates to short-acting calcium channel blocking compounds represented by Formulas (I), (I-a), (I-a-1), and (I-a-2) and their use in treating ischemic heart conditions such as angina pectoris and cardiac arrythmias such as paroxysmal supraventricular tachycardia, atrial flutter and atrial fibrillation in humans. The compounds may also be used to treat other cardiovascular disorders and conditions involving hypertension and blood flow.

Accordingly, the first aspect of the invention features compounds having a structure according to Formula (I)

or a pharmaceutically acceptable addition salt thereof, where each linker a, b, c, d, and e is, independently, $CH_2$, O, S, or a single bond;

linker f is C(O) or a single bond;

each $R_1$, $R_2$, $R_3$, $R_4$, and $R_5$ is, independently, H, F, Cl, Br, substituted or unsubstituted lower alkyl, substituted or unsubstituted lower alkoxyalkyl, or $CO_2R_9$;

each $R_6$ and $R_7$ is, independently, H, substituted or unsubstituted lower alkyl, or substituted or unsubstituted lower alkoxyalkyl;

$R_8$ is H, substituted or unsubstituted lower alkyl, substituted or unsubstituted aryl, or substituted or unsubstituted lower alkoxyalkyl;

$R_9$ is substituted or unsubstituted lower alkyl, substituted or unsubstituted lower alkoxyalkyl, substituted or unsubstituted aryl, substituted or unsubstituted heteroaryl, substituted or unsubstituted aralkyl, or substituted or unsubstituted heteroaralkyl;

n is 2, 3, or 4, where any combination of 0, 1, or 2 methyl or ethyl groups in total can be substituted on any of the methylene groups in the chain; and where when any $R_1$, $R_2$, $R_3$, $R_4$, or $R_5$ is H, F, Cl, or Br, the corresponding linker is a single bond.

In some embodiments, at least one of a-$R_1$, b-$R_2$, c-$R_3$, d-$R_4$, or e-$R_5$ is (single bond)-$CO_2R_9$ or at least one of $R_1$, $R_2$, $R_3$, $R_4$, or $R_5$ is a lower alkyl substituted with $CO_2R_9$ or is a lower alkoxyalkyl substituted with $CO_2R_9$. In a desirable embodiment, n is 2, $R_8$ is substituted or unsubstituted lower alkyl or substituted or unsubstituted lower alkoxyalkyl and at least one of a-$R_1$, b-$R_2$, c-$R_3$, d-$R_4$, or e-$R_5$ is (single bond)-$CO_2R_9$ or at least one of $R_1$, $R_2$, $R_3$, $R_4$, or $R_5$ is a lower alkyl substituted with $CO_2R_9$ or is a lower alkoxyalkyl substituted with $CO_2R_9$.

In some embodiments, e-$R_5$ is (single bond)-H.

In other embodiments, the structure according to Formula (I) is the hydrochloric acid or the oxalic acid addition salt thereof.

In the second aspect, the invention features pharmaceutical compositions that include a compound having a structure according to Formula (I)

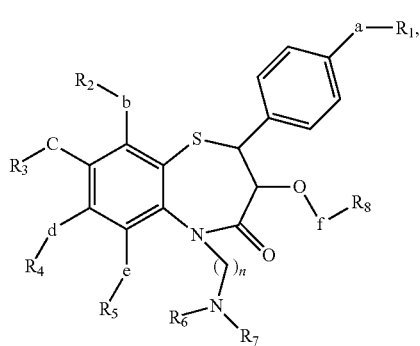

(I)

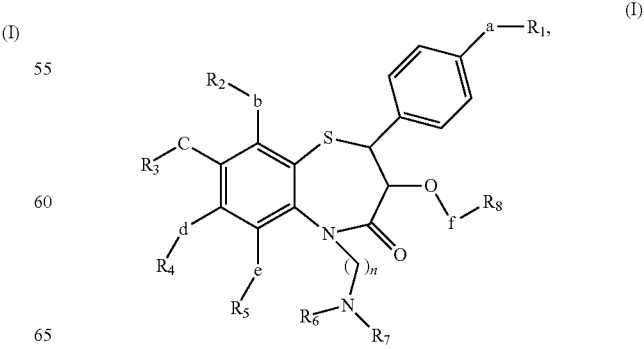

(I)

or a pharmaceutically acceptable addition salt thereof, where each linker a, b, c, d, and e is, independently, $CH_2$, O, S, or a single bond;

linker f is C(O) or a single bond;

each $R_1$, $R_2$, $R_3$, $R_4$, and $R_5$ is, independently, H, F, Cl, Br, substituted or unsubstituted lower alkyl, substituted or unsubstituted lower alkoxyalkyl, or $CO_2R_9$;

each $R_6$ and $R_7$ is, independently, H, substituted or unsubstituted lower alkyl, or substituted or unsubstituted lower alkoxyalkyl;

$R_8$ is H, substituted or unsubstituted lower alkyl, substituted or unsubstituted aryl, or substituted or unsubstituted lower alkoxyalkyl;

$R_9$ is substituted or unsubstituted lower alkyl, substituted or unsubstituted lower alkoxyalkyl, substituted or unsubstituted aryl, substituted or unsubstituted heteroaryl, substituted or unsubstituted aralkyl, or substituted or unsubstituted heteroaralkyl;

n is 2, 3, or 4, where any combination of 0, 1, or 2 methyl or ethyl groups in total can be substituted on any of the methylene groups in the chain; and where when any $R_1$, $R_2$, $R_3$, $R_4$, or $R_5$ is H, F, Cl, or Br, the corresponding linker is a single bond.

In some embodiments, at least one of a-$R_1$, b-$R_2$, c-$R_3$, d-$R_4$, or e-$R_5$ is (single bond)-$CO_2R_9$ or at least one of $R_1$, $R_2$, $R_3$, $R_4$, or $R_5$ is a lower alkyl substituted with $CO_2R_9$ or is a lower alkoxyalkyl substituted with $CO_2R_9$. In a desirable embodiment, n is 2, $R_8$ is substituted or unsubstituted lower alkyl or substituted or unsubstituted lower alkoxyalkyl and at least one of a-$R_1$, b-$R_2$, c-$R_3$, d-$R_4$, or e-$R_5$ is (single bond)-$CO_2R_9$ or at least one of $R_1$, $R_2$, $R_3$, $R_4$, or $R_5$ is a lower alkyl substituted with $CO_2R_9$ or is a lower alkoxyalkyl substituted with $CO_2R_9$.

In some embodiments, e-$R_5$ is (single bond)-H.

In other embodiments, the pharmaceutical composition includes the hydrochloric acid or the oxalic acid addition salt of the compound according to Formula (I).

In some embodiments, the pharmaceutical composition is formulated for treating an ischemic heart condition or cardiac arrhythmia. In some embodiments, the ischemic heart condition is stable angina, unstable angina, or vasospastic angina. In a desirable embodiment, the ischemic heart condition is stable angina. In another desirable embodiment, the ischemic heart condition is unstable angina. In certain embodiments, the composition is included in a kit with instructions for administration.

In some embodiments, the pharmaceutical composition is formulated for treating a hypertensive crisis in an emergency room setting. In certain embodiments, the composition is included in a kit with instructions for administration.

In other embodiments, the pharmaceutical composition is formulated for treating hypertension before, during or after surgery, or no-reflow phenomenon following reperfusion. In certain embodiments, the composition is included in a kit with instructions for administration.

In still other embodiments, the pharmaceutical composition is formulated for treating a method of treating a disease associated with decreased skeletal muscle blood flow. In certain embodiments, the composition is included in a kit with instructions for administration.

In certain embodiments, the pharmaceutical composition is formulated for parenteral (e.g., intravenous or intramuscular) administration.

Accordingly, the third aspect of the invention features a method of treating an ischemic heart condition or cardiac arrhythmia. This method includes administering to a patient in need thereof a therapeutically effective amount of a compound having a structure according to Formula (I)

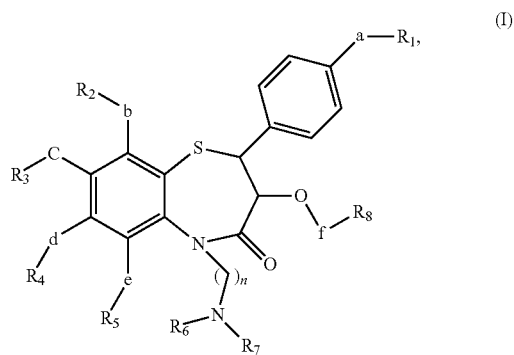

or a pharmaceutically acceptable addition salt or pharmaceutical composition thereof, where each linker a, b, c, d, and e is, independently, $CH_2$, O, S, or a single bond;

linker f is C(O) or a single bond;

each $R_1$, $R_2$, $R_3$, $R_4$ and $R_5$ is, independently, H, F, Cl, Br, substituted or unsubstituted lower alkyl, substituted or unsubstituted lower alkoxyalkyl, or $CO_2R_9$;

each $R_6$ and $R_7$ is, independently, H, substituted or unsubstituted lower alkyl, or substituted or unsubstituted lower alkoxyalkyl;

$R_8$ is H, substituted or unsubstituted lower alkyl, substituted or unsubstituted aryl, or substituted or unsubstituted lower alkoxyalkyl;

$R_9$ is substituted or unsubstituted lower alkyl, substituted or unsubstituted lower alkoxyalkyl, substituted or unsubstituted aryl, substituted or unsubstituted heteroaryl, substituted or unsubstituted aralkyl, or substituted or unsubstituted heteroaralkyl;

n is 2, 3, or 4, where any combination of 0, 1, or 2 methyl or ethyl groups in total can be substituted on any of the methylene groups in the chain; and where when any $R_1$, $R_2$, $R_3$, $R_4$, or $R_5$ is H, F, Cl, or Br, the corresponding linker is a single bond.

In some embodiments, at least one of a-$R_1$, b-$R_2$, c-$R_3$, d-$R_4$, or e-$R_5$ is (single bond)-$CO_2R_9$ or at least one of $R_1$, $R_2$, $R_3$, $R_4$, or $R_5$ is a lower alkyl substituted with $CO_2R_9$ or is a lower alkoxyalkyl substituted with $CO_2R_9$. In a desirable embodiment, n is 2, $R_8$ is substituted or unsubstituted lower alkyl or substituted or unsubstituted lower alkoxyalkyl and at least one of a-$R_1$, b-$R_2$, c-$R_3$, d-$R_4$, or e-$R_5$ is (single bond)-$CO_2R_9$ or at least one of $R_1$, $R_2$, $R_3$, $R_4$, or $R_5$ is a lower alkyl substituted with $CO_2R_9$ or is a lower alkoxyalkyl substituted with $CO_2R_9$.

In some embodiments, e-$R_5$ is (single bond)-H.

In some embodiments, the hydrochloric acid or the oxalic acid addition salt of the compound of Formula (I) is administered to the patient in need thereof. In still other embodiments, the compound of Formula (I), or a pharmaceutically acceptable addition salt or pharmaceutical composition thereof, is administered parenterally (e.g., via intravenous or intramuscular injection).

In another embodiment of the third aspect of the invention, the ischemic heart condition is stable angina, unstable angina, or vasospastic angina. In a desirable embodiment, the ischemic heart condition is stable angina. In a further desirable embodiment of the first aspect of the invention, the cardiac arrhythmia is atrial fibrillation, atrial flutter, paroxysmal supraventricular tachycardia (PSVT), premature atrial, nodal, or ventricular depolarizations, atrial tachycardia, ventricular tachycardia, ventricular fibrillation, or Torsades de Pointes. Desirably, in the first aspect of the invention, administering includes intramuscular, sublingual, buccal, transdermal, intranasal or inhalation administration and the patient desirably is a human patient.

In the fourth aspect, the invention features another method of treating a hypertensive crisis in an emergency room setting. This method involves administering to a patient in need thereof a therapeutically effective amount of a compound having the a structure according to Formula (I)

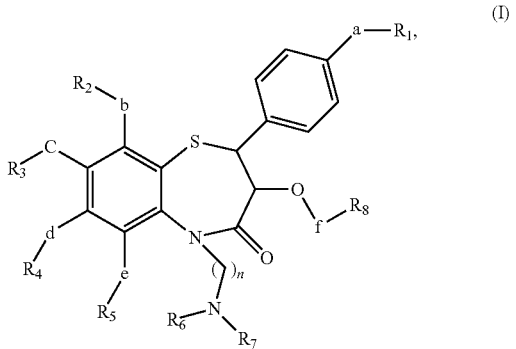

or a pharmaceutically acceptable addition salt or pharmaceutical composition thereof, where each linker a, b, c, d, and e is, independently, $CH_2$, O, S, or a single bond;

linker f is C(O) or a single bond;

each $R_1$, $R_2$, $R_3$, $R_4$, and $R_5$ is, independently, H, F, Cl, Br, substituted or unsubstituted lower alkyl, substituted or unsubstituted lower alkoxyalkyl, or $CO_2R_9$;

each $R_6$ and $R_7$ is, independently, H, substituted or unsubstituted lower alkyl, or substituted or unsubstituted lower alkoxyalkyl;

$R_8$ is H, substituted or unsubstituted lower alkyl, substituted or unsubstituted aryl, or substituted or unsubstituted lower alkoxyalkyl;

$R_9$ is substituted or unsubstituted lower alkyl, substituted or unsubstituted lower alkoxyalkyl, substituted or unsubstituted aryl, substituted or unsubstituted heteroaryl, substituted or unsubstituted aralkyl, or substituted or unsubstituted heteroaralkyl;

n is 2, 3, or 4, where any combination of 0, 1, or 2 methyl or ethyl groups in total can be substituted on any of the methylene groups in the chain; and where when any $R_1$, $R_2$, $R_3$, $R_4$, and $R_5$ is H, F, Cl, or Br, the corresponding linker is a single bond.

In some embodiments, at least one of a-$R_1$, b-$R_2$, c-$R_3$, d-$R_4$, or e-$R_5$ is (single bond)-$CO_2R_9$ or at least one of $R_1$, $R_2$, $R_3$, $R_4$, or $R_5$ is a lower alkyl substituted with $CO_2R_9$ or is a lower alkoxyalkyl substituted with $CO_2R_9$. In a desirable embodiment, n is 2, $R_8$ is substituted or unsubstituted lower alkyl or substituted or unsubstituted lower alkoxyalkyl, and at least one of a-$R_1$, b-$R_2$, c-$R_3$, d-$R_4$, or e-$R_5$ is (single bond)-$CO_2R_9$ or at least one of $R_1$, $R_2$, $R_3$, $R_4$, or $R_5$ is a lower alkyl substituted with $CO_2R_9$ or is a lower alkoxyalkyl substituted with $CO_2R_9$.

In some embodiments, e-$R_5$ is (single bond)-H.

Desirably, in the fourth aspect of the invention, administering includes sublingual, buccal, intranasal, inhalation, or parenteral administration. Desirably, parenteral administration is intravenous or intramuscular administration. In a further desirable embodiment of the fourth aspect of the invention, the patient is a human patient.

In some embodiments, the hydrochloric acid or the oxalic acid addition salt of the compound of Formula (I), or a pharmaceutical composition thereof, is administered to the patient.

The fifth aspect of the invention features another method of treating hypertension before, during or after surgery, or no-reflow phenomenon following reperfusion. This method involves administering to a patient in need thereof a therapeutically effective amount of a compound having the a structure according to Formula (I)

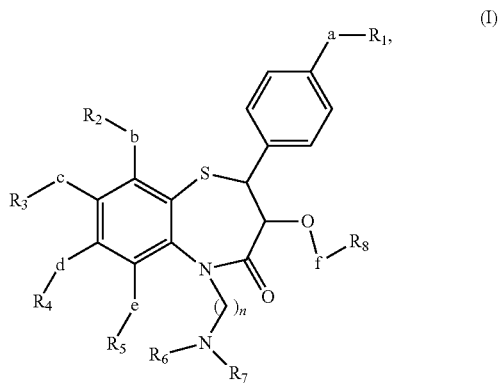

or a pharmaceutically acceptable addition salt or pharmaceutical composition thereof, where each linker a, b, c, d, and e is, independently, $CH_2$, O, S, or a single bond;

linker f is C(O) or a single bond;

each $R_1$, $R_2$, $R_3$, $R_4$, and $R_5$ is, independently, H, F, Cl, Br, substituted or unsubstituted lower alkyl, substituted or unsubstituted lower alkoxyalkyl, or $CO_2R_9$;

each $R_6$ and $R_7$ is, independently, H, substituted or unsubstituted lower alkyl, or substituted or unsubstituted lower alkoxyalkyl;

$R_8$ is H, substituted or unsubstituted lower alkyl, substituted or unsubstituted aryl, or substituted or unsubstituted lower alkoxyalkyl;

$R_9$ is substituted or unsubstituted lower alkyl, substituted or unsubstituted lower alkoxyalkyl, substituted or unsubstituted aryl, substituted or unsubstituted heteroaryl, substituted or unsubstituted aralkyl, or substituted or unsubstituted heteroaralkyl;

n is 2, 3, or 4, where any combination of 0, 1, or 2 methyl or ethyl groups in total can be substituted on any of the methylene groups in the chain; and where when any $R_1$, $R_2$, $R_3$, $R_4$ or $R_5$ is H, F, Cl, or Br, the corresponding linker is a single bond.

In some embodiments, at least one of a-$R_1$, b-$R_2$, c-$R_3$, or e-$R_5$ is (single bond)-$CO_2R_9$ or at least one of $R_1$, $R_2$, $R_3$, $R_4$, or $R_5$ is a lower alkyl substituted with $CO_2R_9$ or is a lower alkoxyalkyl substituted with $CO_2R_9$. In a desirable embodiment, n is 2, $R_8$ is substituted or unsubstituted lower alkyl or substituted or unsubstituted lower alkoxyalkyl and at least one of a-$R_1$, b-$R_2$, c-$R_3$, d-$R_4$, or e-$R_5$ is (single bond)-$CO_2R_9$ or at least one of $R_1$, $R_2$, $R_3$, $R_4$, or $R_5$ is a lower alkyl substituted with $CO_2R_9$ or is a lower alkoxyalkyl substituted with $CO_2R_9$.

In some embodiments, e-$R_5$ is (single bond)-H.

In another desirable embodiment of the fifth aspect of the invention, administering includes parenteral administration, and parenteral administration desirably is intravenous or intramuscular administration. In a further desirable embodiment of the fifth aspect of the invention, the patient is a human patient.

In some embodiments, the hydrochloric acid or the oxalic acid addition salt of the compound of Formula (I), or a pharmaceutical composition thereof, is administered to the patient.

The sixth aspect of the invention features another method of treating a disease associated with decreased skeletal muscle blood flow. This method involves administering to a patient in need thereof a therapeutically effective amount of a compound having the a structure according to Formula (I)

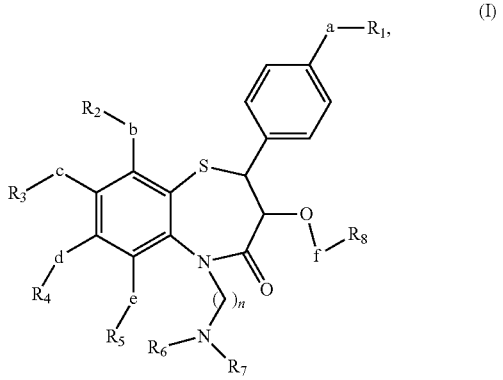

(I)

or a pharmaceutically acceptable addition salt or pharmaceutical composition thereof, where each linker a, b, c, d, and e is, independently, $CH_2$, O, S, or a single bond;

linker f is C(O) or a single bond;

each $R_1$, $R_2$, $R_3$, $R_4$, and $R_5$ is, independently, H, F, Cl, Br, substituted or unsubstituted lower alkyl, substituted or unsubstituted lower alkoxyalkyl, or $CO_2R_9$;

each $R_6$ and $R_7$ is, independently, H, substituted or unsubstituted lower alkyl, or substituted or unsubstituted lower alkoxyalkyl;

$R_8$ is H, substituted or unsubstituted lower alkyl, substituted or unsubstituted aryl, or substituted or unsubstituted lower alkoxyalkyl;

$R_9$ is substituted or unsubstituted lower alkyl, substituted or unsubstituted lower alkoxyalkyl, substituted or unsubstituted aryl, substituted or unsubstituted heteroaryl, substituted or unsubstituted aralkyl, or substituted or unsubstituted heteroaralkyl;

n is 2, 3, or 4, where any combination of 0, 1, or 2 methyl or ethyl groups in total can be substituted on any of the methylene groups in the chain; and where when any $R_1$, $R_2$, $R_3$, $R_4$ or $R_5$ is H, F, Cl, or Br, the corresponding linker is a single bond.

In some embodiments, at least one of a-$R_1$, b-$R_2$, c-$R_3$, d-$R_4$, or e-$R_5$ is (single bond)-$CO_2R_9$ or at least one of $R_1$, $R_2$, $R_3$, $R_4$, or $R_5$ is a lower alkyl substituted with $CO_2R_9$ or is a lower alkoxyalkyl substituted with $CO_2R_9$. In a desirable embodiment, n is 2, $R_8$ is substituted or unsubstituted lower alkyl or substituted or unsubstituted lower alkoxyalkyl and at least one of a-$R_1$, b-$R_2$, c-$R_3$, d-$R_4$, or e-$R_5$ is (single bond)-$CO_2R_9$ or at least one of $R_1$, $R_2$, $R_3$, $R_4$, or $R_5$ is a lower alkyl substituted with $CO_2R_9$ or is a lower alkoxyalkyl substituted with $CO_2R_9$.

In some embodiments, e-$R_5$ is (single bond)-H.

In other desirable embodiments of the sixth aspect of the invention, the disease associated with decreased skeletal muscle blood flow is Raynaud's phenomenon or intermittent claudication. Desirably, in the fourth aspect of the invention, administering includes intramuscular, sublingual, buccal, transdermal, intranasal, inhalation or topical administration. In a further desirable embodiment of the sixth aspect of the invention, the patient is a human patient.

In some embodiments, the hydrochloric acid or the oxalic acid addition salt of the compound of Formula (I) is administered to the patient in need thereof. In still other embodiments, the compound of Formula (I), or a pharmaceutically acceptable addition salt or pharmaceutical composition thereof, is administered parenterally (e.g., via intravenous or intramuscular injection).

The seventh aspect of the invention features a method of treating hypertension in a patient. This method includes administering to a patient in need thereof a therapeutically effective amount of a compound having the a structure according to Formula (I)

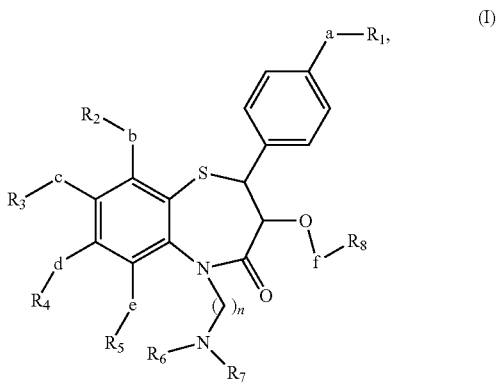

(I)

or a pharmaceutically acceptable addition salt or pharmaceutical composition thereof, where each linker a, b, c, d, and e is, independently, $CH_2$, O, S, or a single bond;

linker f is C(O) or a single bond;

each $R_1$, $R_2$, $R_3$, $R_4$, and $R_5$ is, independently, H, F, Cl, Br, substituted or unsubstituted lower alkyl, substituted or unsubstituted lower alkoxyalkyl, or $CO_2R_9$;

each $R_6$ and $R_7$ is, independently, H, substituted or unsubstituted lower alkyl, or substituted or unsubstituted lower alkoxyalkyl;

$R_8$ is H, substituted or unsubstituted lower alkyl, substituted or unsubstituted aryl, or substituted or unsubstituted lower alkoxyalkyl;

$R_9$ is substituted or unsubstituted lower alkyl, substituted or unsubstituted lower alkoxyalkyl, substituted or unsubstituted aryl, substituted or unsubstituted heteroaryl, substituted or unsubstituted aralkyl, or substituted or unsubstituted heteroaralkyl;

n is 2, 3, or 4, where any combination of 0, 1, or 2 methyl or ethyl groups in total can be substituted on any of the methylene groups in the chain; and where when any $R_1$, $R_2$, $R_3$, $R_4$, and $R_5$ is H, F, Cl, or Br, the corresponding linker is a single bond.

In some embodiments, at least one of a-$R_1$, b-$R_2$, c-$R_3$, d-$R_4$, or e-$R_5$ is (single bond)-$CO_2R_9$ or at least one of $R_1$, $R_2$, $R_3$, $R_4$, or $R_5$ is a lower alkyl substituted with $CO_2R_9$ or is a lower alkoxyalkyl substituted with $CO_2R_9$. In a desirable embodiment, n is 2, $R_8$ is substituted or unsubstituted lower alkyl or substituted or unsubstituted lower alkoxyalkyl and at least one of a-$R_1$, b-$R_2$, c-$R_3$, d-$R_4$, or e-$R_5$ is (single bond)-$CO_2R_9$ or at least one of $R_1$, $R_2$, $R_3$, $R_4$, or $R_5$ is a lower alkyl substituted with $CO_2R_9$ or is a lower alkoxyalkyl substituted with $CO_2R_9$.

In some embodiments, e-$R_5$ is (single bond)-H.

In a desirable embodiment, treatment of hypertension does not occur immediately prior to, during, or after a surgical procedure. In another desirable embodiment of the seventh aspect of the invention, administering includes parenteral administration, and parenteral administration desirably is intravenous or intramuscular administration. In a further desirable embodiment of the seventh aspect of the invention, the patient is a human patient.

In some embodiments, the hydrochloric acid or the oxalic acid addition salt of the compound of Formula (I), or a pharmaceutical composition thereof, is administered to the patient.

In any of the methods of the invention, the compound, or pharmaceutically acceptable salt or pharmaceutical composition thereof, can be administered to a patient over a time period that is 1, 2, 3, 4, 5, 6, or 7 days. In some embodiments, the compound is administered daily. In other embodiments, the compound is administered 1, 2, 3, 4, 5, 6, 7, 8, 9, 10, 11, or 12 times per day.

In any of the methods of the invention, the compound, or pharmaceutically acceptable salt or pharmaceutical composition thereof, can be administered to a patient over a time period that is 1, 2, 3, 4, 5, 6, 7, 8, 9, 10, 11, or 12 weeks.

In any of the methods of the invention, the compound, or pharmaceutically acceptable salt or pharmaceutical composition thereof, can be administered to a patient over a time period that is 1, 2, 3, 4, 5, 6, 7, 8, 9, 10, 11, or 12 months.

In any of the methods of the invention, the compound, or pharmaceutically acceptable salt or pharmaceutical composition thereof, can be administered to a patient over a time period that is 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 years.

In any of the methods of the invention, the compound, or a pharmaceutically acceptable salt or pharmaceutical composition thereof, can be administered daily. In some embodiments, administration occurs 1, 2, 3, 4, 5, 6, 7, 8, 9, 10, 11, or 12 times per day.

In any of the methods of the invention, the amount of compound, or pharmaceutically acceptable salt or pharmaceutical composition thereof, that is administered may vary during the time period of administration.

In any of the methods of the invention, administration of the compound of Formula (I), or pharmaceutically acceptable salt or pharmaceutical composition thereof, is parenteral (e.g., intramuscular) administration.

The pharmaceutical compositions disclosed herein may be included in a kit with instructions for administration according to the methods of the invention.

In any of the compounds, pharmaceutical compositions, kits, and methods of the invention, Formula (I) can exclude any of the structures selected from the group consisting of:

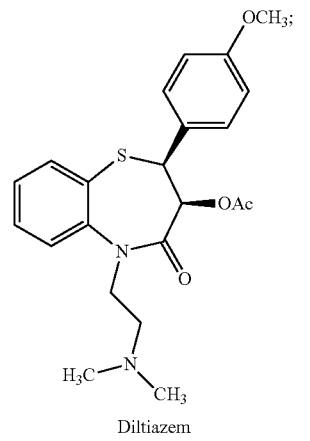

Diltiazem

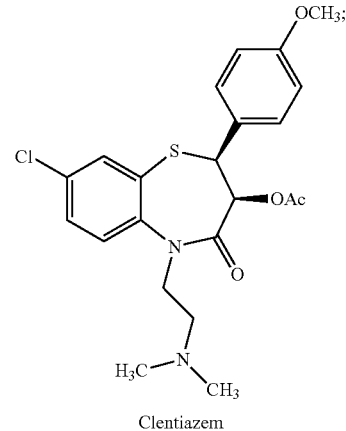

Clentiazem

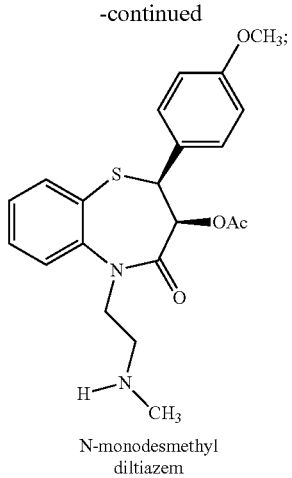
N-monodesmethyl diltiazem
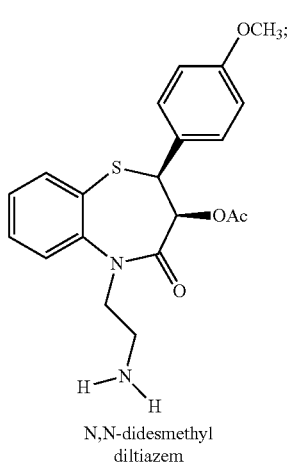
N,N-didesmethyl diltiazem
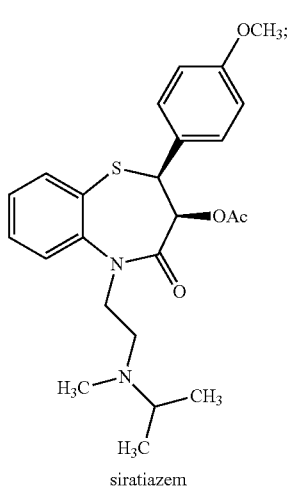
siratiazem
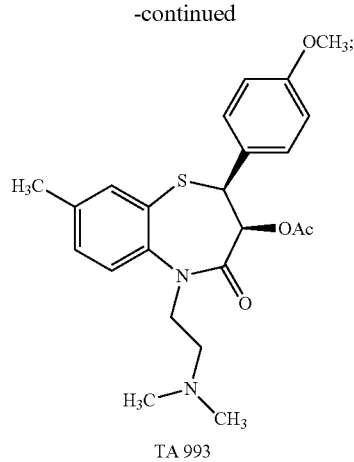
TA 993
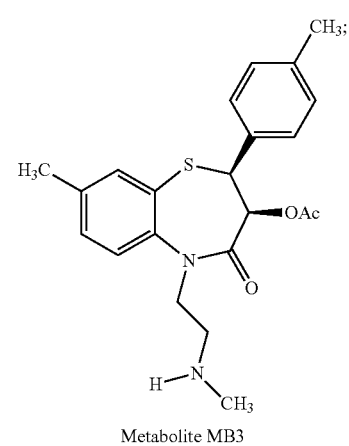
Metabolite MB3
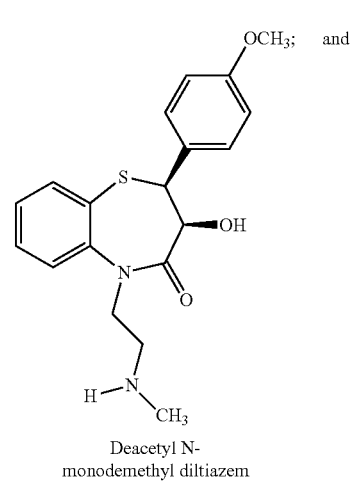
Deacetyl N-monodemethyl diltiazem -continued

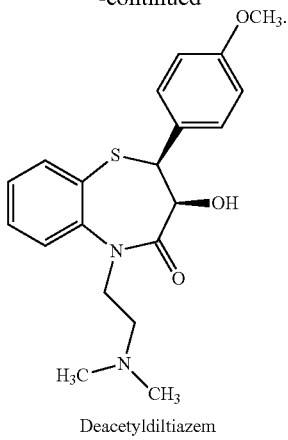

Deacetyldiltiazem

In any of the methods, pharmaceutical compositions, or kits of the invention, the compound used in the invention may be stereochemically pure or may be used as a mixture of stereochemical isomers. In some embodiments, the compound is racemic. In other embodiments, the compound is a single enantiomer or a single diastereomer. In still other embodiments, the compound is a mixture of diastereomers or a mixture of enantiomers.

In any of the compounds, pharmaceutical compositions, kits, and methods of the invention, the compound of Formula (I) can have the following structure

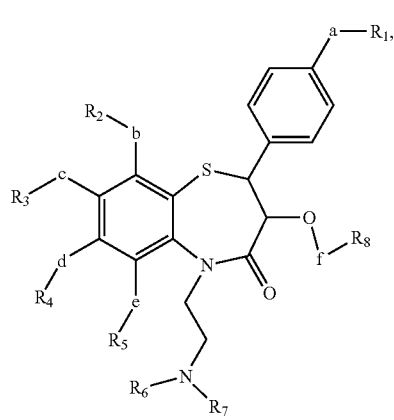

(I-a)

wherein each a, b, c, d, e, f, $R_1$, $R_2$, $R_3$, $R_4$, $R_5$, $R_6$, $R_7$, and $R_8$ has the same meaning as in Formula (I).

In any of the compounds, pharmaceutical compositions, kits, and methods of the invention, the compound of Formula (I) can have the following structure

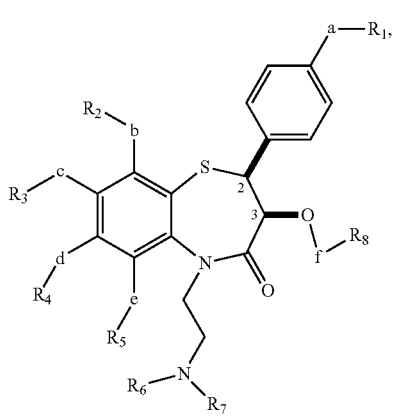

(I-a-1)

or a pharmaceutically acceptable salt thereof.

In Formula (I-a-1), each linker a, b, c, d, and e is, independently, $CH_2$, O, S, or a single bond;

linker f is C(O) or a single bond;

each $R_1$, $R_2$, $R_3$, $R_4$, and $R_5$ is, independently, H, F, Cl, Br, substituted or unsubstituted lower alkyl, substituted or unsubstituted lower alkoxyalkyl, or $CO_2R_9$;

each $R_6$, $R_7$, and $R_8$ is, independently, H, substituted or unsubstituted lower alkyl, or substituted or unsubstituted lower alkoxyalkyl;

$R_9$ is substituted or unsubstituted lower alkyl, substituted or unsubstituted lower alkoxyalkyl, substituted or unsubstituted aryl, substituted or unsubstituted heteroaryl, substituted or unsubstituted aralkyl, substituted or unsubstituted heteroaralkyl;

where when any $R_1$, $R_2$, $R_3$, $R_4$ and $R_5$ is H, F, Cl, or Br, the corresponding linker is a single bond; and at least one of a-$R_1$, b-$R_2$, c-$R_3$, d-$R_4$, or e-$R_5$ is (single bond)-$CO_2R_9$ or at least one of $R_1$, $R_2$, $R_3$, $R_4$, or $R_5$ is a lower alkyl substituted with $CO_2R_9$ or is a lower alkoxyalkyl substituted with $CO_2R_9$; and the $C_6H_4$-a-$R_1$ group at C2 and the O-f-$R_3$ group at C3 are cis to one another.

In some embodiments, e-$R_5$ is (single bond)-H.

In some embodiments, the compound of Formula (I-a) has the following structure:

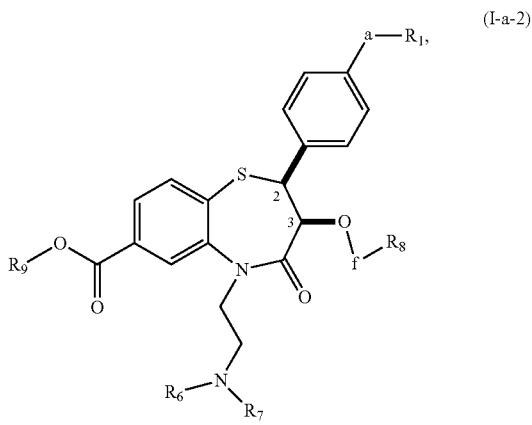

(I-a-2)

or a pharmaceutically acceptable salt thereof, wherein each a, f, $R_1$, $R_6$, $R_7$, $R_8$, and $R_9$ has the same meaning as in Formula (I-a).

In some embodiments, the carbons C2 and C3 in Formula (I-a-1) or (I-a-2) each have the S-configuration. In some embodiments, e-$R_5$ is (single bond)-H.

In any of the compounds, pharmaceutical compositions, kits, and methods of the invention, one of a-$R_1$, b-$R_2$, c-$R_3$, d-$R_4$, or e-$R_5$ may be (single bond)-$CO_2R_9$.

In any of the compounds, pharmaceutical compositions, kits, and methods of the invention, $R_9$ can be substituted or unsubstituted lower alkyl.

In any of the compounds, pharmaceutical compositions, kits, and methods of the invention, $R_9$ can be substituted or unsubstituted lower alkoxyalkyl.

In any of the compounds, pharmaceutical compositions, kits, and methods of the invention, a-$R_1$ can be O-(unsubstituted lower alkyl) or O-(substituted lower alkyl).

In any of the compounds, pharmaceutical compositions, kits, and methods of the invention, $R_9$ can be substituted or unsubstituted aryl.

In any of the compounds, pharmaceutical compositions, kits, and methods of the invention, $R_9$ can be substituted or unsubstituted heteroaryl.

In any of the compounds, pharmaceutical compositions, kits, and methods of the invention, $R_9$ can be substituted or unsubstituted aralkyl.

In any of the compounds, pharmaceutical compositions, kits, and methods of the invention, $R_9$ can be substituted or unsubstituted heteroaralkyl In any of the compounds, pharmaceutical compositions, kits, and methods of the invention, a-$R_1$ can be (single bond)-$CO_2R_9$.

In any of the compounds, pharmaceutical compositions, kits, and methods of the invention, b-$R_2$, c-$R_3$, d-$R_4$, or e-$R_5$ can be O-(unsubstituted lower alkyl) or O-(substituted lower alkyl).

In any of the compounds, pharmaceutical compositions, kits, and methods of the invention, b-$R_2$, c-$R_3$, d-$R_4$, or e-$R_5$ can be (single bond)-$CO_2R_9$.

In any of the compounds, pharmaceutical compositions, kits, and methods of the invention, $R_6$ and $R_7$ can be, independently, substituted or unsubstituted lower alkyl.

In any of the compounds, pharmaceutical compositions, kits, and methods of the invention, f-$R_8$ is C(O)-(unsubstituted lower alkyl) or C(O)-(substituted lower alkyl).

In any of the compounds, pharmaceutical compositions, kits, and methods of the invention, a lower alkyl or a lower alkoxyalkyl may be unsubstituted.

In any of the compounds, pharmaceutical compositions, kits, and methods of the invention, a lower alkyl or a lower alkoxyalkyl may be substituted at any carbon position. In some embodiments, the substituted lower alkyl or the substituted lower alkoxyalkyl may have 1, 2, 3, 4, 5, 6, 7, 8, or 9 substituents. In some embodiments, a lower alkyl or a lower alkoxyalkyl is substituted with —$CO_2$(lower alkyl), —$CO_2$(lower alkoxyalkyl), or halogen. In some embodiments, the halogen is chlorine or fluorine.

In any of the compounds, pharmaceutical compositions, kits, and methods of the invention, a lower alkyl may be: methyl, ethyl, propyl, isopropyl, n-butyl, s-butyl, i-butyl, t-butyl, pentyl, isoamyl, hexyl, heptyl, cyclopropyl, cyclobutyl, cyclopentyl, cyclohexyl, cyclobutylmethyl, or cycloheptyl. In some embodiments, a lower alkyl is methyl, ethyl, propyl, isopropyl, n-butyl, t-butyl, or cyclopropyl.

In any of the compounds, pharmaceutical compositions, kits, and methods of the invention, a lower alkyl substituted with —$CO_2$(lower alkyl) may be: —$CH_2CO_2R_{10}$, —$CH_2CH_2CO_2R_{10}$, —$CH(CO_2R_{10})CH_3$, —$CH_2CH_2CH_2CO_2R_{10}$, —$CH(CO_2R_{10})CH_2CH_3$, —$CH_2CH(CO_2R_{10})CH_3$, —$CH(CH_3)CH_2CO_2R_{10}$, —$C(CH_3)_2CO_2R_{10}$, —$CH_2CH_2CH_2CH_2CO_2R_{10}$, —$CH_2CH_2CH_2CH_2CH_2CO_2R_{10}$, —$CH_2CH_2CH_2CH_2CH_2CH_2CO_2R_{10}$, or —$CH_2CH_2CH_2CH_2CH_2CH_2CH_2CO_2R_{10}$, where $R_{10}$ is a lower alkyl. In some embodiments, $R_{10}$ is methyl, ethyl, propyl, isopropyl, t-butyl, or cyclopropyl. In other embodiments, a lower alkyl substituted with —$CO_2$(lower alkyl) is: —$CH_2CO_2CH_3$, —$CH_2CO_2CH_2CH_3$, —$CH_2CH_2CO_2CH_3$, or —$CH_2CH_2CO_2CH_2CH_3$.

In any of the compounds, pharmaceutical compositions, kits, and methods of the invention, a lower alkoxyalkyl may be: —$CH_2OR_{11}$, —$CH_2CH_2OR_{11}$, —$CH(OR_{11})CH_3$, —$CH_2CH_2CH_2OR_{11}$, —$CH(OR_{11})CH_2CH_3$, —$CH_2CH(OR_{11})CH_3$, —$CH(CH_3)CH_2OR_{11}$, —$C(CH_3)_2OR_{11}$, —$CH_2CH_2CH_2CH_2COR_{11}$, —$CH_2CH_2CH_2CH_2CH_2OR_{11}$, —$CH_2CH_2CH_2CH_2CH_2CH_2OR_{11}$, or —$CH_2CH_2CH_2CH_2CH_2CH_2CH(OR_{11})$, where $R_{11}$ is a lower alkyl. In some embodiments, $R_{11}$ is methyl, ethyl, propyl, isopropyl, n-butyl, t-butyl, or cyclopropyl. In other embodiments, a lower alkoxyalkyl is —$CH_2OCH_3$, —$CH_2OCH_2CH_3$, —$CH_2CH_2OCH_3$, or —$CH_2CH_2OCH_2CH_3$.

In any of the compounds, pharmaceutical compositions, kits, and methods of the invention, a lower alkyl substituted with —$CO_2$(lower alkoxyalkyl) may be: —$CH_2CO_2R_{12}$, —$CH_2CH_2CO_2R_{12}$, —$CH(CO_2R_{12})CH_3$, —$CH_2CH_2CH_2CO_2R_{12}$, —$CH(CO_2R_{12})CH_2CH_3$, —$CH_2CH(CO_2R_{12})CH_3$, —$CH(CH_3)CH_2CO_2R_{12}$, —$C(CH_3)_2CO_2R_{12}$, —$CH_2CH_2CH_2CH_2CO_2R_{12}$, —$CH_2CH_2CH_2CH_2CH_2CO_2R_{12}$, —$CH_2CH_2CH_2CH_2CH_2CH_2CO_2R_{12}$, or -$CH_2CH_2CH_2CH_2CH_2CH_2CH_2(CO_2R_{12})$, where $R_{12}$ is a lower alkoxyalkyl. In some embodiments, $R_{12}$ is $CH_2CH_2OCH_3$ or $CH_2CH_2OCH_2CH_3$. In other embodiments, a lower alkyl substituted with —$CO_2$(lower alkoxyalkyl) is: —$CH_2CO_2(CH_2CH_2OCH_3)$, —$CH_2CO_2(CH_2CH_2OCCH_2CH_3)$, —$CH_2CH_2CO_2(CH_2CH_2OCH_3)$, or —$CH_2CH_2CO_2(CH_2CH_2OCCH_2CH_3)$.

In any of the compounds, pharmaceutical compositions, kits, and methods of the invention, a lower alkyl substituted with halogen may be: —$CH_2X$, —$CHX_2$, —$CX_3$, —$CH_2CX_3$, —$CX_2CX_3$, or —$CH(CX_3)_2$, where each X is, independently, —F, —Cl, —Br, or —I. In some embodiments, X is selected from —F or —Cl. In some embodiments, a lower alkyl substituted with fluorine or chlorine is —$CF_3$, —$CCl_3$, —$CF_2CF_3$, or —$CH(CF_3)_2$.

In any of the compounds, pharmaceutical compositions, kits, and methods of the invention, a lower alkoxyalkyl substituted with —$CO_2$(lower alkyl) may be: —$CH_2CH(CO_2R_{13})OR_{14}$, —$CH(CO_2R_{13})CH_2OR_{14}$, —$CH_2CH_2OCH_2CH_2(CO_2R_{13})$, or —$CH_2CH_2OCH(CO_2R_{13})CH_3$, where $R_{13}$ and $R_{14}$ are each, independently, lower alkyl. In some embodiments, $R_{13}$ is methyl, ethyl, propyl, isopropyl, t-butyl, or cyclopropyl. In some embodiments, $R_{14}$ is methyl, ethyl, propyl, isopropyl, n-butyl, t-butyl, or cyclopropyl.

In any of the compounds, pharmaceutical compositions, kits, and methods of the invention, a lower alkoxyalkyl substituted with —$CO_2$(lower alkoxyalkyl) may be: —$CH_2CH(CO_2R_{15})OR_{16}$, —$CH(CO_2R_{15})CH_2OR_{16}$, —$CH_2CH_2OCH_2CH_2(CO_2R_{15})$, or —$CH_2CH_2OCH(CO_2R_{15})CH_3$, where, independently, $R_{15}$ is a lower alkoxyalkyl and $R_{16}$ is a lower alkyl. In some embodiments, $R_{15}$ is $CH_2CH_2OCH_3$ or $CH_2CH_2OCH_2CH_3$. In some embodiments, $R_{16}$ is methyl, ethyl, propyl, isopropyl, n-butyl, t-butyl, or cyclopropyl.

In any of the compounds, pharmaceutical compositions, kits, and methods of the invention, a lower alkoxyalkyl substituted with halogen may be: —CX₂CX₂OCH₂CH₃, —CH₂CH₂OCH₂CX₃, —CH₂CH₂OCX₂CX₃, or —CH₂CH₂OCH(CX₃)₂, where X is —F, —Cl, —Br, or —I. In some embodiments, X is —F or —Cl.

In any of the compounds, pharmaceutical compositions, kits, and methods of the invention, a aralkyl can be benzyl(—CH₂C₆H₅) or phenethyl(—CH₂CH₂C₆H₅). Where the benzyl or phenethyl groups are substituted, any hydrogen in the group can be replaced with a substituent group as described herein. For example, a substituted benzyl or phenethyl group may have 1, 2, 3, 4, 5, 6, or 7 substituents. Exemplary substituents include hydroxyl, halogen (—F, —Cl, —Br, or —I), —CN, —NO₂, unsubstituted lower alkyl, substituted lower alkyl (e.g., lower alkyl substituted with halogen), unsubstituted lower alkoxy, substituted lower alkoxy, unsubstituted lower alkoxyalkyl, substituted lower alkoxyalkyl, or CO₂R₁₇, where R₁₇ is unsubstituted or substituted lower alkyl or unsubstituted or substituted lower alkoxyalkyl).

In any of the compounds, methods, pharmaceutical compositions, or kits of the invention, CO₂R₉ may be: CO₂CH₃, CO₂CH₂CH₃, CO₂CH(CH₃)₂, CO₂C(CH₃)₃, CO₂CH₂CH₂OCH₃, CO₂CH₂CH₂OCH₂CH₃, or CO₂CH₂C₆H₅.

In any of the compounds, pharmaceutical compositions, kits, and methods of the invention, e-R₅ can be (single bond)-H.

In any of the compounds, methods, pharmaceutical compositions, or kits of the invention, the compound is selected from:

-continued

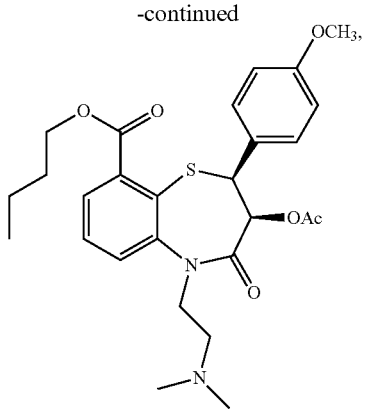

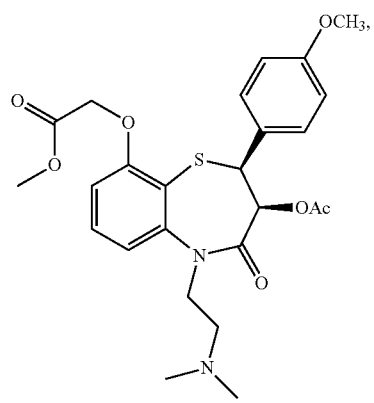

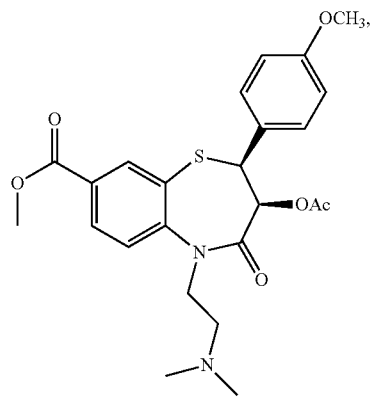

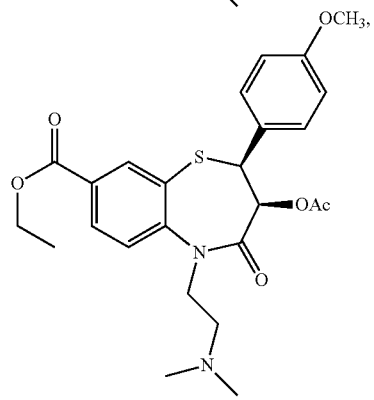

-continued
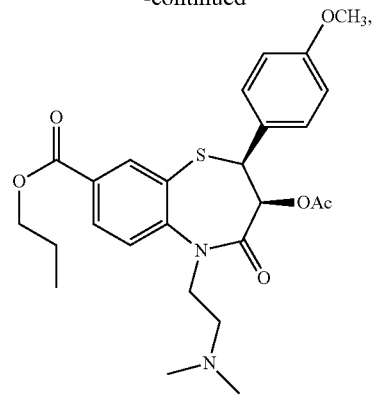
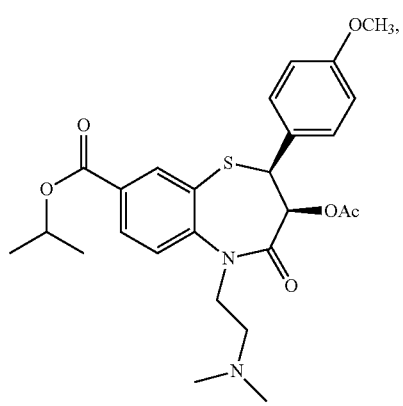
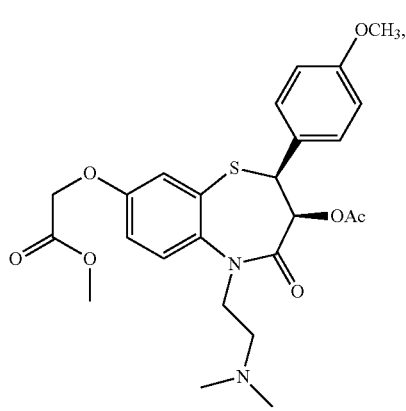
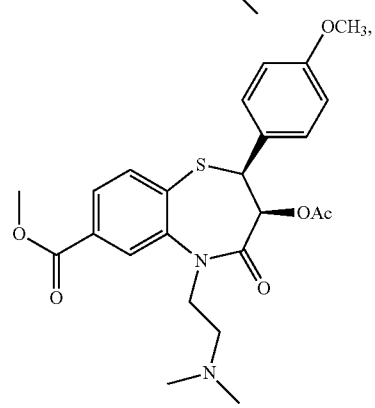
-continued
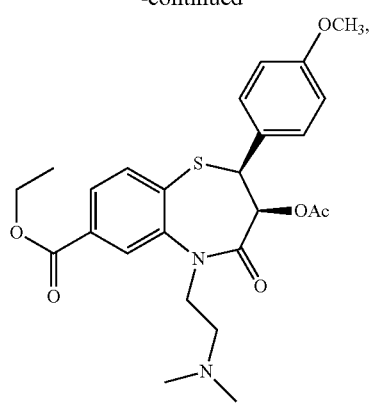
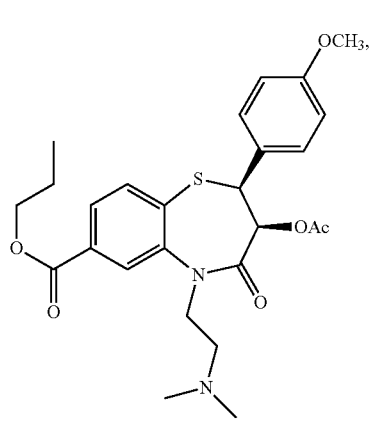
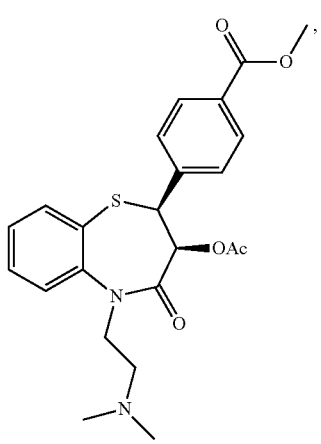
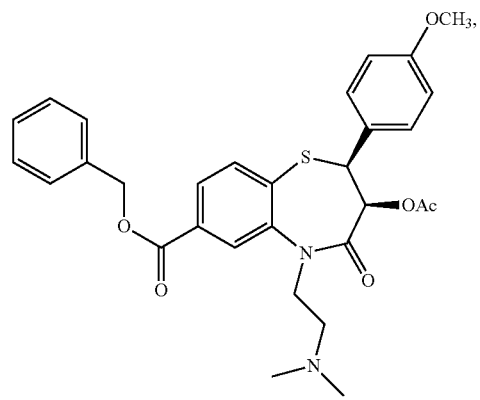

-continued

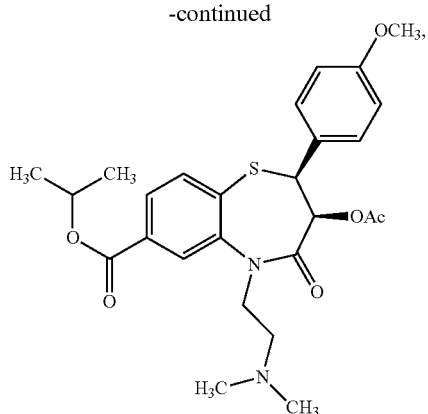

DEFINITIONS

As used herein, the term "angina" refers to the chest discomfort felt due to ischemic heart disease. Angina can be classified as stable angina whose principal underlying cause is arteriosclerosis, vasospastic angina (also called variant angina or Prinzmetal angina) whose underlying cause is due to transient vasospasm of the coronary arteries, or unstable angina caused by platelet clotting at sites of ruptured arteriosclerotic plaques.

As used herein, the term "aralkyl" means a lower alkyl group where one of the hydrogens is substituted with aryl (e.g., benzene, naphthalene, anthracene, or phenanthrene). Exemplary aralkyl groups include benzyl and phenethyl. Aralkyl groups may be unsubstituted or substituted with, for example, 1, 2, 3, 4, 5, 6, or 7 substituent groups located at any position (i.e., on the $sp^2$ or the $sp^3$ hybridized carbons of the group).

As used herein, the term "aryl" means an optionally substituted $C_6$-$C_{14}$ cyclic group with [4n+2] π electrons in conjugation and where n is 1, 2, or 3. Non-limiting examples of arenes include heteroaryls and benzene, naphthalene, anthracene, and phenanthrene. Aryls may be unsubstituted or substituted. A substituted aryl may be optionally substituted with 1, 2, 3, 4, 5, or 6 substituents located at any position of the ring.

As used herein, the term "buccal administration" means absorption of a compound or a pharmaceutically acceptable formulation of a compound by administering between the cheek and gum. The compound is, for example, a compound of Formula (I), (I-a), (I-a-1), or (I-a-2).

As used herein, "carbonyl" refers to a group in which a carbon has a double bond to oxygen. A carbonyl group may be represented using C(O) or C=O.

"Cardiac arrhythmia" as used herein, refers to a condition characterized by abnormal heart rhythms that are irregular, too fast, too slow, or conducted via an abnormal electrical pathway through the heart. Arrhythmias can be divided into ventricular arrhythmias occurring in the lower chambers of the heart (ventricles) and into supraventricular arrhythmias occurring in the upper chambers of the heart (aorta). Cardiac arrhythmias include atrial fibrillation and atrial flutter that are characterized by abnormally fast electrical discharge patterns that cause the atria to contract very rapidly thereby impairing efficient pumping of the blood into the ventricles. Cardiac arrhythmias also include paroxysmal supraventricular tachycardia (PSVT) that is characterized by a regular and fast heart rate originating in heart tissue above the ventricles. Other exemplary cardiac arrhythmias are premature atrial, nodal, or ventricular depolarization, atrial tachycardia, ventricular tachycardia, ventricular fibrillation, and Torsades de Pointes.

A "disease associated with decreased skeletal muscle blood flow" as used herein refers to a condition where a narrowing of the arteries that perfuse the skeletal muscle results in reduced perfusion and oxygen delivery. Such conditions include, but are not limited to, Raynaud's phenomenon and intermittent claudication.

The term "excipient" is used herein to describe any ingredient other than an active compound (e.g., those having Formula I) described herein. Excipients may include, for example: antiadherents, antioxidants, binders, coatings, compression aids, disintegrants, dyes (colors), emollients, emulsifiers, fillers (diluents), film formers or coatings, flavors, fragrances, glidants (flow enhancers), lubricants, preservatives, printing inks, sorbents, suspensing or dispersing agents, sweeteners, or waters of hydration. Exemplary excipients include, but are not limited to: benzalconium chloride, butylated hydroxytoluene (BHT), calcium carbonate, calcium phosphate (dibasic), calcium stearate, capric acid, chitosan, citric acid, cod liver oil extract, croscarmellose, crosslinked polyvinyl pyrrolidone, crospovidone, cyclodextrins, cysteine, ethyl benzoate, ethylcellulose, gelatin, glyceryl monooleate, glyceryl monostearate, hydroxypropyl cellulose, hydroxypropyl methylcellulose, lactose, laureth-9, lauric acid, lecithin, magnesium stearate, maltitol, mannitol, methionine, methyl benzoate, methylcellulose, methyl paraben, microcrystalline cellulose, octoxynol-9, EDTA, oleic acid, polyacrylic acids, polyethylene glycol, polyoxyethylene-23-lauryl ether, polysorbate, polyvinyl pyrrolidone, povidone, pregelatinized starch, propyl paraben, retinyl palmitate, shellac, silicon dioxide, sodium carboxymethyl cellulose, sodium cholate, sodium citrate, sodium deoxycholate, sodium dodecylsulfate, sodium fusidate, sodium glycocholate, sodium glycodeoxycholate, sodium starch glycolate, sodium taurocholate, sorbitol, starch (corn), stearic acid, sucrose, talc, titanium dioxide, triethyl citrate, trimethyl citrate, vitamin A, vitamin E, vitamin C, and xylitol.

As used herein, the term "heteroaralkyl" means a lower alkyl group where one of the hydrogens is substituted with heteroaryl. Heteroaralkyl groups may be unsubstituted or substituted with, for example, 1, 2, 3, 4, 5, 6, or 7 substituent groups.

As used herein, "heteroaryl" refers to an aryl group that contains 1, 2, or 3 heteroatoms in the cyclic framework. Exemplary heteroaryls include, but are not limited to, furan, thiophene, pyrrole, thiadiazole (e.g., 1,2,3-thiadiazole or 1,2,4-thiadiazole), oxadiazole (e.g., 1,2,3-oxadiazole or 1,2,5-oxadiazole), oxazole, benzoxazole, isoxazole, isothiazole, pyrazole, thiazole, benzthiazole, triazole (e.g., 1,2,4-triazole or 1,2,3-triazole), benzotriazole, pyridines, pyrimidines, pyrazines, quinoline, isoquinoline, purine, pyrazine, pteridine, triazine (e.g, 1,2,3-triazine, 1,2,4-triazine, or 1,3,5-triazine)indoles, 1,2,4,5-tetrazine, benzo[b]thiophene, benzo[c]thiophene, benzofuran, isobenzofuran, and benzimidazole. Heteroaryls may be unsubstituted or substituted with 1, 2, 3, 4, 5, or 6 subsitutents.

"Hypertension before, during or after surgery" as used herein refers to perioperative hypertension, i.e., a sustained elevated blood pressure (systolic/diastolic $\geq$140/90 mm Hg in the USA, or $\geq$160/95 mm Hg in many other countries) that occurs immediately prior to, during, or after a surgical procedure.

The term "hypertensive crisis in an emergency room setting" as used herein refers to a sudden increase in systolic and diastolic blood pressures that requires immediate management in a hospital or hospital emergency room environment. The sudden acute and severe increase in blood pressure may or may not be associated with acute end-organ damage (i.e., cardiovascular, renal, central nervous system).

"Inhalation administration" or "administration by inhalation" as used herein refers to delivering a drug (e.g., a compound of Formula (I), (I-a), (I-a-1), or (I-a-2)) for absorption to the body in the form of a liquid aerosol mist, solid aerosol particulates or a gaseous substance by inhalation into the lungs.

As used herein, the term "intranasal administration" or "nasal administration" means absorption of a compound or a pharmaceutically acceptable formulation of a compound by administering to the nose or nasal cavity. The compound may be, for example, a compound of Formula (I), (I-a), (I-a-1), or (I-a-2).

As used herein, the term "intravenous administration" means injection of a pharmaceutically acceptable formulation of a compound (e.g., a compound of Formula (I), (I-a), (I-a-1), or (I-a-2)) directly into a vein.

The term "ischemic heart disease" or "ischemic heart condition" as used herein refers to a condition characterized by narrowed heart arteries that results in restricted blood flow and reduced oxygen delivery to the heart muscle.

The term "lower alkoxy" as used herein means a group having the structure —OR, where R is a substituted or unsubstituted lower alkyl or a substituted or unsubstituted lower alkoxyalkyl.

The term "lower alkoxyalkyl" as used herein means a lower alkyl group having an ether-containing substituent such as, for example, ethoxyethyl, methoxyethyl, and methoxypropyl, among others, where the ether-containing substituent may be at any position of the lower alkyl. A lower alkoxyalkyl may be, for example: —CH$_2$OR$_{11}$, —CH$_2$CH$_2$OR$_{11}$, —CH(OR$_{11}$)CH$_3$, —CH$_2$CH$_2$CH$_2$OR$_{11}$, —CH(OR$_{11}$)CH$_2$CH$_3$, —CH$_2$CH(OR$_{11}$)CH$_3$, —CH(CH$_3$)CH$_2$OR$_{11}$, —C(CH$_3$)$_2$OR$_{11}$, —CH$_2$CH$_2$CH$_2$COR$_{11}$, —CH$_2$CH$_2$CH$_2$CH$_2$OR$_{11}$, —CH$_2$CH$_2$CH$_2$CH$_2$CH$_2$OR$_{11}$, or —CH$_2$CH$_2$CH$_2$CH$_2$CH$_2$CH$_2$CH(OR$_{11}$), where R$_{11}$ is a lower alkyl. Desirably, R$_{11}$ is methyl, ethyl, propyl, isopropyl, n-butyl, t-butyl, or cyclopropyl. Exemplary, non-limiting lower alkoxyalkyls include —CH$_2$OCH$_3$, —CH$_2$OCH$_2$CH$_3$, —CH$_2$CH$_2$OCH$_3$, and —CH$_2$CH$_2$OCH$_2$CH$_3$. A lower alkoxyalkyl may be optionally substituted. A substituted lower alkoxyalkyl may be optionally substituted, for example, with CO$_2$R$_9$ at any carbon position on either the lower alkyl group or at any carbon position on the ether containing substituent.

The term "lower alkyl" as used herein means alkyl groups of from 1 to 7 carbon atoms that consist of a straight, branched or cyclic configuration. Lower alkyls may include 1, 2, 3, 4, 5, 6, or 7 carbon atoms. Examples of lower alkyl groups include, but are not limited to: methyl, ethyl, propyl, isopropyl, butyl, s-, i- and t-butyl, pentyl, isoamyl, hexyl, heptyl, cyclopropyl, cyclobutyl, cyclopentyl, cyclohexyl, cyclobutylmethyl, and cycloheptyl, among others. Desirably, a lower alkyl is methyl, ethyl, propyl, isopropyl, n-butyl, t-butyl, or cyclopropyl. A lower alkyl may be optionally substituted. A substituted lower alkyl may be optionally substituted with, for example, CO$_2$R$_9$ at any carbon position.

As used herein, "no-reflow phenomenon following reperfusion" refers to the inability of myocardial tissue to reperfuse after prolonged ischemia despite reopening of the occluded artery related to the ischemic condition.

As used herein "parenteral administration" means administration of a compound or a pharmaceutically acceptable formulation of a compound by a route that bypasses the gastrointestinal tract. Desirably parenteral administration is intravenous administration, injection of a pharmaceutically acceptable formulation of a compound below the skin's cutaneous layer (subcutaneous), within the dermis (intradermal), or into the muscle (intramuscular). The compound may be, for example, a compound of Formula (I), (I-a), (I-a-1), or (I-a-2).

The term "pharmaceutically acceptable formulation" as used herein refers to a composition including a pharmaceutically acceptable carrier and an active compound. The compound may be, for example, a compound of Formula (I), (I-a), (I-a-1), or (I-a-2).

A "pharmaceutically acceptable carrier" as used herein refers to a vehicle capable of suspending or dissolving the active compound, and having the properties of being nontoxic and non-inflammatory in a patient. Moreover, a pharmaceutically acceptable carrier may include a pharmaceutically acceptable additive, such as a preservative, antioxidant, fragrance, emulsifier, dye, or excipient known or used in the field of drug formulation and that does not significantly interfere with the therapeutic effectiveness of the biological activity of the active agent, and that is non-toxic to the patient.

As used herein, the term "pharmaceutical patch" refers to a pad containing an embedded active compound to be placed on the exterior surface of a patient for absorption of the active compound into the bloodstream, skin or underlying tissue. Desirably, patch is placed on the skin and the compound is released gradually from the patch over time. Further, the patch desirably is an adhesive patch.

As used herein a "pharmaceutically acceptable acid addition salt" is derived from a basic active compound and an organic acid or an inorganic acid. Exemplary pharmaceutically acceptable acid addition salts derived from organic acids include acetate, adipate, alginate, ascorbate, aspartate, benzenesulfonate, benzoate, butyrate, camphorate, camphersulfonate, citrate, cyclopentanepropionate, digluconate, dodecylsulfate, ethanesulfonate, fumarate, glucoheptonate, glycerophosphate, heptonate, hexanoate, 2-hydroxy-ethanesulfonate, isethionate, lactobionate, lactate, laurate, lauryl sulfate, malate, maleate, malonate, methanesulfonate (mesylate), 2-naphthalenesulfonate, nicotinate, oleate, oxalate, palmitate, pamoate, pectinate, persulfate, 3-phenylpropionate, picrate, pivalate, propionate, stearate, succinate, tartrate, thiocyanate, toluenesulfonate, undecanoate, and valerate salts, and the like. Exemplary pharmaceutically acceptable acid addition salts derived from inorganic acids include bisulfate, sulfate, borate, hydrobromide, hydrochloride, hydroiodide, hemisulfate, nitrate, phosphate salts and the like. Desirably, a "pharmaceutically acceptable acid addition salt" is hydrochloride, hydrobromide, methanesulfonate, sulfate, hemisulfate or bisulfate.

As used herein, the term "sublingual administration" means absorption of a compound or a pharmaceutically acceptable formulation of a compound by administering under the tongue. The compound may be, for example, a compound of Formula (I), (I-a), (I-a-1), or (I-a-2).

As used herein, the term "therapeutically effective amount" refers to an amount of an active compound that, when administered to a patient, reduces, eliminates or prevents an ischemic heart condition, hypertensive crisis in an emergency room setting, hypertension before, during or after surgery, no-reflow phenomenon following reperfusion, or a disease associated with decreased skeletal muscle bloodflow. Desirably, a therapeutically effective amount of a pharmaceutical formulation contains a compound of, for example, Formula (1), (1-a), (I-a-1), or (I-a-2), in a concentration range of about 0.000001 to 10 percent weight/volume ("% w/v").

As used herein, "topical administration" or "topically administering" refers to the application of a pharmaceutical acceptable formulation of a compound to the external surface of a patient, such that the active compound enters the underlying tissue. Desirably, the external surface is the skin and topical administration desirably involves application of a pharmaceutically acceptable formulation to intact skin, to broken skin, to raw skin or to an open skin wound. The compound is, for example, a compound of Formula (I), (I-a), (I-a-1), or (I-a-2).

"Transdermal administration" or "transdermally administering" as used herein refers to the diffusion of an agent across the barrier of the skin resulting from topical administration or other application of a compound or a pharmaceutically acceptable formulation of a compound. The compound is, for example, a compound of Formula (I), (I-a), (I-a-1), or (I-a-2).

Where a group may be optionally substituted, optional substituents include, but are not limited to: hydroxy(—OH), —CN, —NO$_2$, halogen (i.e., —F, —Cl, —Br, or —I), —CO$_2$H, —CO$_2$(lower alkyl), —CO$_2$(lower alkoxyalkyl), -(lower alkyl), -(lower alkoxyalkyl), —O(lower alkyl), —O(lower alkoxyalkyl), —NH(lower alkyl), —NH(lower alkoxyalkyl), —N(lower alkyl)$_2$, and —N(lower alkoxyalkyl)$_2$. In some embodiments, a substituted group may have 1, 2, 3, 4, 5, 6, 7, 8, or 9 substituents located at any position. In some embodiments, a substituent group that includes lower alkyl or lower alkoxy is further substituted.

These definitions and others stated in The Merck Manual 16$^{th}$ edition 1992 (Chapter 25 pp 461-498, Chapter 25 pp 498-507, Chapter 24 pp 413-429) and Goodman and Gilman's "The Pharmacological Basis of Therapeutics" 11$^{th}$ edition 2006 (Chapter 34 pp 899-908, Chapter 31 pp 823-824 and pp 830-832, Chapter 32 pp 845-846) are herein incorporated in these definitions.

Other features and advantages of the invention will be apparent from the following Detailed Description and the Claims.

DETAILED DESCRIPTION OF THE INVENTION

The present invention relates to the use of a pharmaceutically effective amount of a short-acting calcium channel blocking compound to treat ischemic heart conditions, cardiac arrhythmias, hypertensive crisis in an emergency room setting, hypertension before, during, or after surgery, no-reflow phenomenon following reperfusion, and diseases associated with decreased skeletal muscle blood flow. The compounds used in the methods of the present invention are rendered short-acting by covalent attachment of esterase sensitive groups to molecules derived from the benzothiazepine (e.g., diltiazem) class of calcium channel blockers and may be formulated for sublingual, buccal, transdermal, intranasal, inhalation, topical, and parenteral (e.g., intravenous or intramuscular) routes of administration. Pharmaceutical compositions containing the compounds disclosed herein may be included in a kit with instructions for administration according to the methods of the invention.

In the context of this invention, a short acting calcium channel blocking compound is meant to infer a compound that produces the desired effect and is then rapidly inactivated metabolically. A short acting CCB is meant to have a duration of action of from less than 1 minute to less than 30 minutes. Preferably the compound's duration of action will be from 30 seconds to 20 minutes.

The compounds used in the methods of the present invention are further defined structurally in Formula (I).

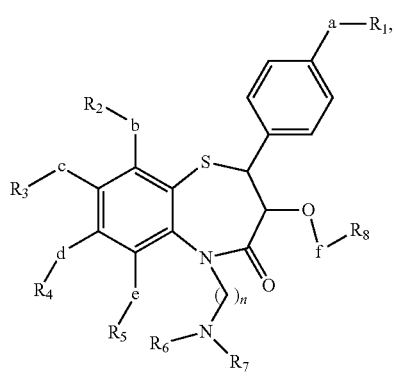

or a pharmaceutically acceptable addition salt thereof, where each linker a, b, c, d, and e is, independently, $CH_2$, O, S, or a single bond;

linker f is C(O) or a single bond;

each $R_1$, $R_2$, $R_3$, $R_4$, and $R_5$ is, independently, H, F, Cl, Br, substituted or unsubstituted lower alkyl, substituted or unsubstituted lower alkoxyalkyl, or $CO_2R_9$;

each $R_6$ and $R_7$ is, independently, H, substituted or unsubstituted lower alkyl, or substituted or unsubstituted lower alkoxyalkyl;

$R_8$ is H, substituted or unsubstituted lower alkyl, substituted or unsubstituted aryl, or substituted or unsubstituted lower alkoxyalkyl;

$R_9$ is substituted or unsubstituted lower alkyl, substituted or unsubstituted lower alkoxyalkyl, substituted or unsubstituted aryl, substituted or unsubstituted heteroaryl, substituted or unsubstituted aralkyl, or substituted or unsubstituted heteroaralkyl;

n is 2, 3, or 4, where any combination of 0, 1, or 2 methyl or ethyl groups in total can be substituted on any of the methylene groups in the chain;

where when any $R_1$, $R_2$, $R_3$, $R_4$ and $R_5$ is H, F, Cl, or Br, the corresponding linker is a single bond.

In a desirable embodiment, n is 2, $R_8$ is substituted or unsubstituted lower alkyl or substituted or unsubstituted lower alkoxyalkyl, and at least one of a-$R_1$, b-$R_2$, c-$R_3$, d-$R_4$, or e-$R_5$ is (single bond)-$CO_2R_9$ or at least one of $R_1$, $R_2$, $R_3$, $R_4$, or $R_5$ is a lower alkyl substituted with $CO_2R_9$ or is a lower alkoxyalkyl substituted with $CO_2R_9$.

In some embodiments, e-$R_5$ is (single bond)-H.

The compounds of Formula (I) also include compounds having a structure according to Formula (I-a)

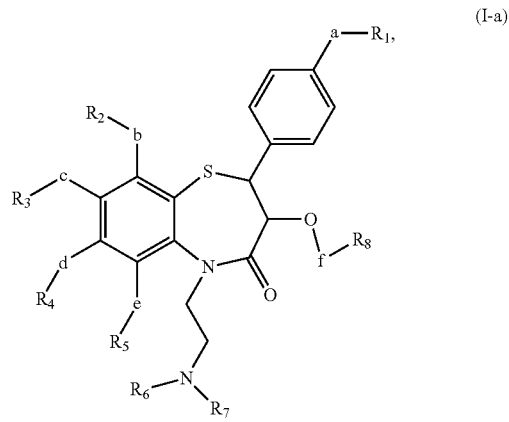

wherein each a, b, c, d, e, f, $R_1$, $R_2$, $R_3$, $R_4$, $R_5$, $R_6$, $R_7$, and $R_8$ has the same meaning as in Formula (I).

The compounds of Formula (I) also include compounds having a structure according to Formula (I-a-1)

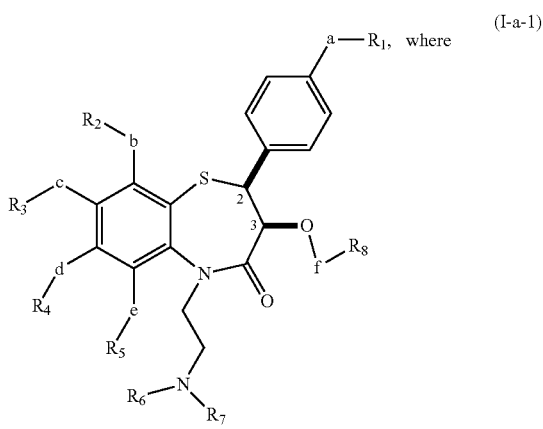

each linker a, b, c, d, and e is, independently, $CH_2$, O, S, or a single bond;

linker f is C(O) or a single bond;

each $R_1$, $R_2$, $R_3$, $R_4$, and $R_5$ is, independently, H, F, Cl, Br, substituted or unsubstituted lower alkyl, substituted or unsubstituted lower alkoxyalkyl, or $CO_2R_9$;

each $R_6$, $R_7$, and $R_8$ is, independently, H, substituted or unsubstituted lower alkyl, or substituted or unsubstituted lower alkoxyalkyl;

$R_9$ is substituted or unsubstituted lower alkyl, substituted or unsubstituted lower alkoxyalkyl, substituted or unsubstituted aryl, substituted or unsubstituted heteroaryl, substituted or unsubstituted aralkyl, or substituted or unsubstituted heteroaralkyl;

where when any $R_1$, $R_2$, $R_3$, $R_4$ and $R_5$ is H, F, Cl, or Br, the corresponding linker is a single bond;

at least one of a-$R_1$, b-$R_2$, c-$R_3$, d-$R_4$, or e-$R_5$ is (single bond)-$CO_2R_9$ or at least one of $R_1$, $R_2$, $R_3$, $R_4$, or $R_5$ is a lower alkyl substituted with $CO_2R_9$ or is a lower alkoxyalkyl substituted with $CO_2R_9$;and the $C_6H_4$-a-$R_1$ group at C2 and the O-f-$R_8$ group at C3 are cis to one another. In some embodiments, the carbons C2 and C3 in Formula (I-a-1) each have the S-configuration. In some embodiments, e-$R_5$ is (single bond)-H.

The compounds of Formula (I) also include compounds having a structure according to Formula (I-a-2):

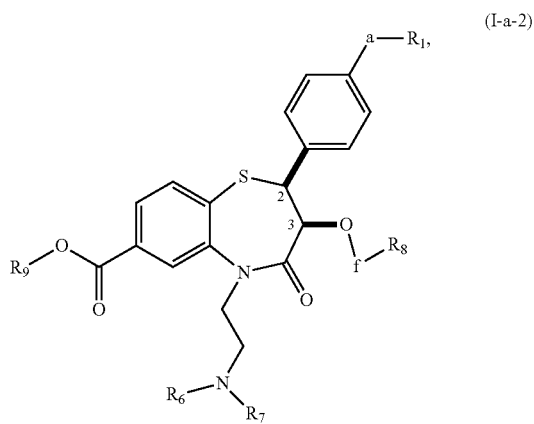

(I-a-2)

or a pharmaceutically acceptable salt thereof, wherein each a, f, $R_1$, $R_6$, $R_7$, $R_8$, and $R_9$ has the same meaning as in Formula (I-a).

The compounds defined by Formulas (I), (I-a), (I-a-1), or (I-a-2) may exist as free bases or as pharmaceutically acceptable acid addition salts.

As described herein, the short-acting calcium channel blockers of the invention (e.g., the compounds of Formula (I), (I-a), (I-a-1), or (I-a-2)) may be used to treat disorders in which the regulation of calcium plays a role in normal hemostasis. Such disorders include, for example, pulmonary hypertension, peripheral vascular disease, mild congestive heart failure, hypertrophic subaortic stenosis, protection against ischemic injury, stroke, migraine, tumor resistance to anti-neoplastic drugs, achalasia, esophageal spasms, bronchial asthma, premature labor, dysmenorrhea, and enhancement of success in renal transplantation.

Pharmaceutical agents, such as a calcium channel-blocking compound, can be made with relatively short durations of therapeutic action, ranging from the ultra-short to medium-range, through non-hepatic means of inactivation. Such agents may be subject to extensive metabolism in blood by serum esterases, as well as potential metabolism in the liver. Rapid elimination or biotransformation to inactive or less active products minimizes accumulation with prolonged or repeated administration. A calcium channel-blocking compound that is rendered sensitive to serum esterases is expected to undergo rapid degradation to inactive or less active metabolites in the blood. This may be considered analogous to the rapid degradation experienced by succinylcholine (Stanski et al., *Anesthesiology* 57: 435-438, 1982) and enables a more predictable correlation of dose with the duration of pharmacologic effect.

Anti-anginal drugs relieve or prevent coronary ischemia by increasing oxygen supply to the heart or by decreasing myocardial oxygen demand. There are three main classes of pharmaceutical agents that are used to treat angina (organic nitrates, calcium channel blockers, and beta-adrenergic antagonists also known as beta-blockers). Organic nitrates (e.g., glyceryl trinitrate, nitroglycerin) are generally effective agents for treating angina and cause vasodilation through release of nitric oxide (NO) to coronary arteries and coronary smooth muscle. However, a major limitation of the use of organic nitrates is the development of nitrate tolerance. Calcium channel blockers (e.g., verapamil, nicardipine, nifedipine, clevidipine, diltiazem, bepredil) antagonize calcium channels in arteriole smooth muscle and cardiac muscle resulting in vasodilation and/or reduced cardiac contractility. Calcium channel blockers are generally well tolerated with minor adverse effects including hypotension, dizziness, edema, nausea, and vomiting, and are contraindicated for patients with hypertrophic obstructive cardiomyopathies.

Medications used to treat atrial fibrillation and slow down the abnormal and rapid heart rate include calcium channel blockers (e.g., verapamil, diltiazem), digoxin (e.g., digitalis), and beta-blockers (e.g., propranolol, atenolol, esmolol). These pharmaceutical agents slow the heart rate by retarding conduction of the electrical discharges through the atrioventricular node, but do not usually convert atrial fibrillation back into a normal rhythm. Other drugs or treatments are necessary to achieve a normal heart rhythm but these are generally associated with greater toxicity.

Calcium channel blockers and beta-blockers are often prescribed for acute pharmacological treatment of atrial flutter as well as traditional antiarrhythmic medications such as amiodarone.

Nitrate containing drugs, such as nitroglycerin or sodium nitroprusside, can be used to address these disorders involving blood flow and pressure regulation, but these drugs can produce rebound tachycardia and other adverse effects. Other traditional hypotensive agents, such as the calcium channel blocker nicardipine, are generally too long acting to effectively address blood pressure regulation surrounding surgery. In contrast, the compounds of Formulas (I), (I-a), (I-a-1), and (I-a-2) are short acting and thus overcome the undesirable characteristics and effects noted above in connection with existing therapies for cardiovascular disorders.

Pharmaceutical Formulations

Desirable routes of administration of the compounds of Formulas (I), (I-a), (I-a-1), and (I-a-2) used in the methods of the present invention include sublingual, buccal, transdermal, intranasal, inhalation, topical, and parenteral (e.g., intravenous, intramuscular, etc.) administration. The compounds of Formulas (I), (I-a), (I-a-1), and (I-a-2) desirably are administered with a pharmaceutically acceptable carrier. Pharmaceutical formulations of the compounds described herein formulated for treatment of the disorders described herein are also part of the present invention.

For a transdermal delivery system, the administration of a therapeutic dose will, of course, be continuous rather than intermittent throughout the dosage regimen.

Dosages for buccal or sublingual administration typically are 0.1 to 500 mg per single dose as required. In practice, the physician determines the actual dosing regimen which is most suitable for an individual patient, and the dosage varies with the age, weight, and response of the particular patient. The above dosages are exemplary of the average case, but individual instances exist wherein higher or lower dosages are merited, and such are within the scope of this invention.

For buccal administration, the compositions may take the form of tablets, lozenges, etc. formulated in a conventional manner. Liquid drug formulations suitable for use with nebulizers and liquid spray devices and electrohydrodynamic (EHD) aerosol devices will typically include a compound of the invention with a pharmaceutically acceptable carrier. Preferably, the pharmaceutically acceptable carrier is a liquid such as alcohol, water, polyethylene glycol or a perfluorocarbon. Optionally, another material may be added to alter the aerosol properties of the solution or suspension of compounds of the invention. Desirably, this material is liquid such as an alcohol, glycol, polyglycol or a fatty acid. Other methods of formulating liquid drug solutions or suspension suitable for use in aerosol devices are known to those of skill in the art (see, e.g., Biesalski, U.S. Pat. No. 5,112,598; Biesalski, U.S. Pat. No. 5,556,611).

The compounds of Formulas (I), (I-a), (I-a-1), and (I-a-2) may also be formulated for nasal administration. For nasal administration, the solutions or suspensions are applied directly to the nasal cavity by conventional means, for example, with a dropper, pipette or spray. The formulations may be provided in a single or multidose form. In the case of a dropper or pipette, dosing may be achieved by the patient administering an appropriate, predetermined volume of the solution or suspension. In the case of a spray, this may be achieved, for example, by means of a metering atomizing spray pump.

The compounds of the invention (for example, compounds having a structure according to Formula (I), (I-a), (I-a-1), and (I-a-2)) may further be formulated for aerosol administration, particularly to the respiratory tract by inhalation and including intranasal administration. The compound will generally have a small particle size for example on the order of five (5) microns or less. Such a particle size may be obtained by means known in the art, for example by micronization. The active ingredient is provided in a pressurized pack with a suitable propellant such as a chlorofluorocarbon (CFC), for example, dichlorodifluoromethane, trichlorofluoromethane, or dichlorotetrafluoroethane, or carbon dioxide or other suitable gas. The aerosol may conveniently also contain a surfactant such as lecithin. The dose of drug may be controlled by a metered valve. Alternatively the active ingredients may be provided in a form of a dry powder, for example, a powder mix of the compound in a suitable powder base such as lactose, starch, and starch derivatives such as hydroxypropylmethyl cellulose, and polyvinylpyrrolidine (PVP). The powder carrier will form a gel in the nasal cavity. The powder composition may be presented in unit dose form for example in capsules or cartridges of e.g., gelatin or blister packs from which the powder may be administered by means of an inhaler.

For human use, a compound of the invention (for example, a compound of Formula (I), (I-a), (I-a-1), or (I-a-2)) can be administered alone, but generally is administered in admixture with a pharmaceutical carrier selected with regard to the intended route of administration and standard pharmaceutical practice. Pharmaceutical compositions for use in accordance with the present invention thus can be formulated in a conventional manner using one or more physiologically acceptable carriers comprising excipients and auxiliaries that facilitate processing of compounds of the invention into preparations which can be used pharmaceutically.

These pharmaceutical compositions can be manufactured in a conventional manner, e.g., by conventional mixing, dissolving, granulating, dragee-making, levigating, emulsifying, encapsulating, entrapping, or lyophilizing processes. Proper formulation is dependent upon the route of administration chosen. The formulation and preparation of such compositions is well-known to those skilled in the art of pharmaceutical formulation.

For administration by inhalation, compounds of the invention (e.g., those having a structure according to Formula (I), (I-a), (I-a-1), or (I-a-2)) are conveniently delivered in the form of an aerosol spray presentation from pressurized packs or a nebulizer, with the use of a suitable propellant. In the case of a pressurized aerosol, the dosage unit can be determined by providing a valve to deliver a metered amount.

Parenteral Formulations

The pharmaceutical formulation may also be administered parenterally (intravenous, intramuscular, subcutaneous or the like) in dosage forms or formulations containing conventional, non-toxic pharmaceutically acceptable carriers and adjuvants. In particular, formulations suitable for parenteral (e.g., intramuscular) administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. For example, to prepare such a composition, compounds of the invention (e.g., compounds of Formula (I), (I-a), (I-a-1), or (I-a-2)) may be dissolved or suspended in a parenterally acceptable liquid vehicle. Among acceptable vehicles and solvents that may be employed are water, water adjusted to a suitable pH by addition of an appropriate amount of hydrochloric acid, sodium hydroxide or a suitable buffer (e.g., phosphoric acid/monosodium phosphate, monosodium phosphate/disodium phosphate, disodium phosphate/trisodium phosphate, citric acid/monosodium citrate, monosodium citrate/disodium citrate, disodium citrate/trisodium citrate, acetic acid/sodium acetate, or benzoic acid/sodium benzoate), 1,3-butanediol, Ringer's solution, isotonic sodium chloride solution, and oils (e.g., sesame, corn, peanut, and cottonseed oils). Water used in parenteral formulations must be sterile and free of particles or pyrogens.

The parenteral formulation may also contain one or more co-solvents (e.g., dimethylsulfoxide (DMSO), ethanol, glycerin, N,N-dimethylacetamide (NMA), N-methyl-2-pyrrolidinone (NMP), propylene glycol, or polyethylene glycol), anti-oxidants (e.g., ascorbic acid, cysteine, monothioglycerol, sodium bisulfite, sodium metabisulfite, or tocopherols), chelating agents (e.g., EDTA and salts thereof), preservatives (e.g., methyl-, ethyl-, or n-propyl p-hydroxybenzoate, benzyl alcohol, benzethonium chloride, chlorobutanol, chlorocresol, metacresol, or phenol), protectants (e.g., glucose, lactose, maltose, sucrose, trehalose, and human serum albumin), solubilizing agents (e.g., cyclodextrins), surfactants (e.g., polyoxyethylene castor oils, egg and soybean phospholipids, lecithin, polysorbate 20 or 80, and sorbitan monooleate), suspending agents (e.g., acacia, carboxymethylcellulose, hydrolyzed gelatin, or povidone), or tonicity adjusting agents (dextrose, glycerin, or NaCl).

The formulations for parenteral administration may be presented in unit-dose or multi-dose containers, for example, sealed ampules and vials, and may be stored in a freeze-dried (lyophilized) conditions requiring only the addition of the sterile liquid carrier, for example, water for injections, immediately prior to use. Extemporaneous injection solutions and suspensions may be prepared from sterile powders, granules and tablets.

Dosages

An active compound (e.g., a compound of Formula (I), (I-a), (I-a-1), or (I-a-2)) may be administered to the patient in a single dose or in multiple doses. When multiple doses are administered, the doses may be separated from one another by, for example, 1-24 hours, 1-7 days, 1-4 weeks, or 1-12 months. The compound may be administered according to a schedule or the compound may be administered without a predetermined schedule (e.g., at the onset of symptoms of angina or at the onset of a hypertensive crisis). An active compound may be administered, for example, 1, 2, 3, 4, 5, 6, 7, 8, 9, 10, 11, or 12 times per day, every $2^{nd}$, $3^{rd}$, $4^{th}$, $5^{th}$, or $6^{th}$ day, 1, 2, 3, 4, 5, 6, or 7 times per week, 1, 2, 3, 4, 5, or 6 times per month, or 1, 2, 3, 4, 5, 6, 7, 8, 9, 10, 11, or 12 times per year. It is to be understood that, for any particular subject, specific dosage regimes should be adjusted over time according to the individual need and the professional judgment of the person administering or supervising the administration of the compositions.

While the attending physician ultimately will decide the appropriate amount and dosage regimen, an effective amount of an active compound (e.g., a compound of Formula (I), (I-a), (I-a-1), or (I-a-2)) may be, for example, in the range of about 0.05 mg to 500 mg/kg body weight. In a desirable embodiment, an effective amount is in the range of about 0.1 mg to 50 mg/kg. For example, an effective amount of a compound can be 0.1, 0.2, 0.3, 0.4, 0.5, 0.6, 0.7, 0.8, 0.9, 1.0, 1.5, 2.5, 3.0, 3.5, 4.0, 4.5, 5.0, 10, 15, 20, 25, 30, 35, 40, 45, or 50 mg/kg body weight.

In the methods of the invention, the time period during which multiple doses of an active compound (for example, a compound having Formula (I), (I-a), (I-a-1), or (I-a-2)) are administered to a patient can vary. For example, in some embodiments doses of the compounds of the invention are administered to a patient over a time period that is 1-7 days; 1-12 weeks; or 1-3 months. In other embodiments, the compounds are administered to the patient over a time period that is, for example, 4-11 months or 1-30 years. In other embodiments, the compounds are administered to a patient at the onset of symptoms. In any of these embodiments, the amount of compound that is administered may vary during the time period of administration. When a compound is administered daily, administration may occur, for example, 1, 2, 3, 4, 5, 6, 7, 8, 9, 10, 11, or 12 times per day.

In still other embodiments, the active compound (e.g., a compound of Formula (I), (I-a), (I-a-1), or (I-a-2)) is administered continuously (e.g., when a compound is administered transdermally or intravenously). Continuous administration refers to uninterrupted administration of a compound for at least 1 hour. For example, the compound can be continuously administered for at least 1, 2, 3, 4, 5, 6, 7, 8, 9, 10, 12, 24, 36, 48, 60, 72, 84, or 96 hours. In other embodiments, continuous administration spans, for example, 1-7 days, 1-12 weeks, 1-12 months, or even 1-30 years. However, the compound may also be continuously administered until the subject is free of the disease being treated.

Topical Pharmaceutical Formulations

Pharmaceutically acceptable topical formulations for use in accordance with the present invention can be formulated in conventional manner using one or more physiologically acceptable carriers comprising excipients and auxiliaries that facilitate processing of the active compounds (e.g., a compound of Formula (I), (I-a), (I-a-1), or (I-a-2)) into preparations that can be used pharmaceutically. Proper formulation is dependent upon the desired product chosen. Non-limiting exemplary formulations are provided below.

The topical formulations useful in the subject invention can be made into a wide variety of product types. These include, but are not limited to, lotions, creams, gels, sticks, sprays, ointments, pastes, mousses, and cosmetics. The product types can include several types of carrier systems including, but not limited to solutions, emulsions, gels, solids, and liposomes. Techniques for formulation and administration are standard in the art and can be found, for example, in "Remington: The Science and Practice of Pharmacy $20^{th}$ edition" Lippincott Williams & Wilkins, Philadelphia, Pa. Eds Gennaro A. R. et al, 2000. The formulation can be selected to maximize delivery to a desired target site in the body such as the skin.

Lotions, which are preparations that are to be applied to the skin surface without friction, are typically liquid or semi-liquid preparations. Lotions may be formulated with an aqueous or oily base and will in general also contain one or more emulsifying agents, stabilizing agents, dispersing agents, suspending agents, thickening agents, or coloring agents.

Creams containing the active agent for delivery according to the present invention are viscous liquid or semisolid emulsions, either oil-in-water or water-in-oil. Cream bases are water-washable, and contain an oil phase, an emulsifier and an aqueous phase. The oil phase, also sometimes called the "internal" phase, generally contains petrolatum and a fatty alcohol such as cetyl or stearyl alcohol; the aqueous phase usually, although not necessarily, exceeds the oil phase in volume, and generally contains a humectant. The emulsifier in a cream formulation, as described in "Remington: The Science and Practice of Pharmacy $20^{th}$ edition" Lippincott Williams & Wilkins, Philadelphia, Pa. Eds Gennaro A. R. et al, 2000, is generally a nonionic, anionic, cationic or amphoteric surfactant.

Gel formulations can also be used in connection with the present invention. As is appreciated by those working in the field of topical drug formulation, gels are semisolid, suspension-type systems. Single-phase gels contain organic macromolecules distributed substantially uniformly throughout the carrier liquid, which is typically aqueous, but also, preferably, contain an alcohol and, optionally, an oil.

Ointments, which are semisolid preparations, are typically based on petrolatum or other petroleum derivatives. As is appreciated by the ordinarily skilled artisan, the specific ointment base to be used is one that provides for optimum delivery for the active agent chosen for a given formulation, and, preferably, provides for other desired characteristics as well, e.g., emolliency or the like. As with other carriers or vehicles, an ointment base should be inert, stable, nonirritating and non-sensitizing. As described, for example, in Remington: The Science and Practice of Pharmacy 20$^{th}$ edition" Lippincott Williams & Wilkins, Philadelphia, Pa. Eds Gennaro A. R. et al, 2000, at pages 845-849, ointment bases may be grouped in four classes: oleaginous bases; absorption bases; water-removable bases; and water-soluble bases. Oleaginous ointment bases include, for example, vegetable oils, fats obtained from animals, and semisolid hydrocarbons obtained from petroleum. Absorption bases, also known as emulsifiable ointment bases, contain little or no water and include, for example, hydroxystearin sulfate, anhydrous lanolin and hydrophilic petrolatum. Absorption bases are either water-in-oil (W/O) emulsions or oil-in-water (O/W) emulsions, and include, for example, cetyl alcohol, glyceryl monostearate, lanolin and stearic acid. Preferred water-soluble ointment bases are prepared from polyethylene glycols of varying molecular weight.

Useful formulations of the invention also encompass sprays. Sprays generally provide the active agent in an aqueous and/or alcoholic solution which can be misted onto the skin for delivery. Such sprays include those formulated to provide for concentration of the active agent solution at the site of administration following delivery, e.g., the spray solution can be primarily composed of alcohol or other like volatile liquid in which the drug or active agent can be dissolved. Upon delivery to the skin, the carrier evaporates, leaving concentrated active agent at the site of administration.

A topical pharmaceutical formulation for use in the present invention may also include suitable solid or gel phase carriers. Examples of such carriers include, but are not limited to, calcium carbonate, calcium phosphate, various sugars, starches, cellulose derivatives, gelatin, and polymers such as polyethylene glycols.

Further, a topical pharmaceutical formulation may include a suitable emulsifier, i.e., an agent that enhances or facilitates mixing and suspending oil-in-water or water-in-oil. An emulsifying agent for use in the invention may consist of a single emulsifying agent or may be a blend of emulsifying agents and may be a nonionic, anionic or cationic surfactant or a blend of two or more such surfactants. Such surface-active agents are described, for example, in "McCutcheon's Detergent and Emulsifiers," North American Edition, 1980 Annual published by the McCutcheon Division, MC Publishing Company, 175 Rock Road, Glen Rock, N.J. 07452, USA.

Especially suitable nonionic emulsifying agents for inclusion in the pharmaceutically acceptable formulations for use in the present invention are those with a hydrophile-lipophile balance (HLB) as determined by the method described, for example, by Paul L. Lindner in "Emulsions and Emulsion", edited by Kenneth Lissant, published by Dekker, New York, N.Y., 1974, pages 188-190. Examples of such nonionic emulsifiers include, but are not limited to, "BRIJ 72," the trade name for a polyoxyethylene (2) stearyl ether having an HLB of 4.9; "BRIJ 721," the trade name for a polyoxyethylene (21) stearyl ether having an HLB of 15.5.

A topical pharmaceutical formulation may also contain suitable emollients. Emollients are materials that may be used for the prevention or relief of dryness, as well as for the protection of the skin. Useful emollients include, but are not limited to, cetyl alcohol, isopropyl myristate, stearyl alcohol, and the like. A wide variety of suitable emollients are known in the art and can be used in the formulations encompassed by the invention. See e.g., Sagarin, Cosmetics, Science and Technology, 2nd Edition, Vol. 1, pp. 32-43 (1972), and U.S. Pat. No. 4,919,934, to Deckner et al., issued Apr. 24, 1990, both of which are incorporated herein by reference in their entirety.

A topical pharmaceutical formulation for use in the methods of the invention may also include suitable antioxidants, i.e., substances that inhibit oxidation. Antioxidants suitable for use in accordance with the present invention include, but are not limited to, butylated hydroxytoluene, ascorbic acid, sodium ascorbate, calcium ascorbate, ascorbic palmitate, butylated hydroxyanisole, 2,4,5-trihydroxybutyrophenone, 4-hydroxymethyl-2,6-di-tert-butylphenol, erythorbic acid, gum guaiac, propyl gallate, thiodipropionic acid, dilauryl thiodipropionate, tert-butylhydroquinone and tocopherols such as vitamin E, and the like, including pharmaceutically acceptable salts and esters of these compounds. Preferably, the antioxidant is butylated hydroxytoluene, butylated hydroxyanisole, propyl gallate, ascorbic acid, pharmaceutically acceptable salts or esters thereof, or mixtures thereof. Most preferably, the antioxidant is butylated hydroxytoluene.

Moreover, topical pharmaceutical formulations for use in the present invention may also include suitable preservatives. Preservatives are compounds added to a pharmaceutical formulation to act as an anti-microbial agent. Among preservatives known in the art as being effective and acceptable in parenteral formulations are benzalkonium chloride, benzethonium, chlorohexidine, phenol, m-cresol, benzyl alcohol, methylparaben, propylparaben, chlorobutanol, o-cresol, p-cresol, chlorocresol, phenylmercuric nitrate, thimerosal, benzoic acid, and various mixtures thereof. See, e.g., Wallhausser, K.-H., Develop. Biol. Standard, 24:9-28 (1974) (S. Krager, Basel).

A topical pharmaceutical formulation for use in the present invention may further contain suitable chelating agents to form complexes with metal cations which do not cross a lipid bilayer. Examples of suitable chelating agents include ethylene diamine tetraacetic acid (EDTA), ethylene glycol-bis (beta-aminoethyl ether)-N,N,N',N'-tetraacetic acid (EGTA) and 8-Amino-2-[(2-amino-5-methylphenoxy)methyl]-6-methoxyquinoline-N,N,N',N'-tetraacetic acid, tetrapotassium salt (QUIN-2).

Topical pharmaceutical formulations useful for the methods of the invention may also include suitable neutralizing agents used to adjust the pH of the formulation to within a pharmaceutically acceptable range. For topical formulations, pH range desirably is 4.5-7.1. Most desirably, the pH range is 4.5-6.5.

Further, a topical pharmaceutical formulation may include suitable hydrophilic gelling agents. These components are, for example, diffusable compounds capable of increasing the viscosity of a polymer-containing solution through the interaction of the agent with the polymer. Also useful herein are hydrophilic gelling agents such as the acrylic acid/ethyl acrylate copolymers and the carboxyvinyl polymers sold by the B. F. Goodrich Company under the trademark of Carbopol® resins. These resins consist essentially of a colloidally water-soluble polyalkenyl polyether crosslinked polymer of acrylic acid crosslinked with from 0.75% to 2.00% of a crosslinking agent such as polyallyl sucrose or polyally pentaerythritol. A desirable viscosity increasing agent is for example Carbopol® Ultrez 10.

A topical pharmaceutical formulation may also contain one or more suitable solvents. Suitable solvents include ethanol, propylene glycol, glycerin, dipropylene glycol and polyethylene glycol. Non-lipophilic drugs typically display very low solubility in pharmaceutically acceptable solvents and/or carriers.

In addition, a topical pharmaceutical formulation for use in the methods of the invention may include one or more suitable skin penetration enhancers. Suitable excipients are known in the art to be skin penetration enhancers (as described, for example, in Osborne D. W. and Henke J. J., "Skin penetration enhancers cited in the technical literature" *Pharm. Tech.* 21:58-66, 1997). Examples of skin penetration enhancers include water, ethanol, propylene glycol, oleic acid, oleyl alcohol, sodium lauryl sulfate, dimethylsulfoxide, 1-dodecylazacycloheptan-2-one (trade name Azone®), N-methyl-2-pyrolidinone, 2-pyrolidinone, D-limonene, 1,8-cineole, urea, and menthol are just a few of the known penetration enhancers. Diethylene glycol monoethyl ether NF (CAS number 111-90-0, NCI name ethoxydiglycol, trade name TRANSCUTOL®) (see, for example, Watkinson A. C. et al., "Aspects of the transdermal delivery of prostaglandins", *Int. J. Pharm.* 74:229-236, 1991; Rojas J. et al., "Optimization of binary and ternary solvent systems in the percutaneous absorption of morphine base", *STP Pharma Sciences,* 1:70-75, 1991; Watkinson A. C., Ph.D. Thesis, University of Wales, 1991; Ritschel W. A. et al., "Development of an intracutaneous depot for drugs. Binding, drug accumulation and retention studies", *Skin Pharmacol.* 4:235-245, 1991).

Diethylene glycol monoethyl ether NF (DGME) is a useful solvent for many drugs, especially non-lipophilic drugs having very low water solubility. In vitro skin absorption studies have shown increased flux values for compounds dissolved in DGME; however, DGME does not fluidize the stratum corneum lipids (Harrison J. E. et al., "The relative effect of Azone and Transcutol on permeant diffusivity and solubility in human stratum corneum," Pharm. Res., 13:542-546, 1996), nor does DGME decrease the lag time associated with the permeant (Rojas J. et al., "Optimization of binary and ternary solvent systems in the percutaneous absorption of morphine base", *STP Pharma Sciences,* 1:70-75, 1991). These additional penetration-enhancing compounds can be used when desired in the pharmaceutical compositions described herein in the conventional range of from about 0.1 to about 10% and preferably about 1.0% to about 5.0% by weight of the topical composition.

Liquid forms, such as lotions suitable for topical administration or suitable for cosmetic application, may include a suitable aqueous or non-aqueous vehicle with buffers, suspending and dispensing agents, thickeners, penetration enhancers, and the like. Solid forms such as creams or pastes or the like may include, for example, any of the following ingredients, water, oil, alcohol or grease as a substrate with surfactant, polymers such as polyethylene glycol, thickeners, solids and the like. Liquid or solid formulations may include enhanced delivery technologies such as liposomes, microsomes, microsponges, patches, and the like.

Topical Administration

The compounds of Formulas (I), (I-a), (I-a-1), and (I-a-2) for use in the methods of the invention can be administered in a pharmaceutically acceptable topical (e.g., transdermal) formulation. Topical treatment regimens according to the practice of the invention may include applying the composition directly to the skin at the application site, from one to several times daily. Also included are delivery methods in the form of pharmaceutical patches.

These formulations may include a pharmaceutically acceptable carrier such as water, oils (including vegetable and mineral oils), cream bases, lotion bases, ointment bases, and the like. These bases include suspending agents, thickeners, penetration enhancers, and the like. Topical and transdermal formulations are well known to those in the art of cosmetics and topical pharmaceuticals and are described, for example, in Chapter 44 of "Remington: The Science and Practice of Pharmacy $20^{th}$ edition" Lippincott Williams & Wilkins, Philadelphia, Pa. Eds Gennaro A. R. et al, 2000, which is incorporated herein by reference.

Topical (e.g., transdermal) formulations may also include pharmaceutically acceptable vehicles. Additives for topical formulations are well-known in the art, and may be added to the topical composition, as long as they are pharmaceutically acceptable and not deleterious to the epithelial cells or their function. Further, the additives should not cause deterioration in the stability of the formulation, in particular, of the active compound. For example, inert fillers, anti-irritants, tackifiers, excipients, fragrances, opacifiers, antioxidants, gelling agents, stabilizers, surfactants, emollients, coloring agents, preservatives, buffering agents, other permeation enhancers, and other conventional components of transdermal delivery devices as are known in the art. Excipients generally are carriers, diluents and/or vehicles used in formulating drug compositions. Excipients are standard in the art and examples of excipients and their application can be found, for instance, in Katz, M. (*Drug Design* 4:93-148, 1973).

Penetration or permeation through the skin of an active compound may be enhanced by an agent (e.g., p20 solvents) or a mixture of agents which, alone or in combination, act to increase the permeability of the skin to a drug. The enhanced permeation effected through the use of such enhancers can be observed, for example, by measuring the rate of diffusion of the drug through animal or human skin using a diffusion cell apparatus. A diffusion cell is described by Merritt et al. "Diffusion Apparatus for Skin Penetration", *J. of Controlled Release,* 1:161-162, 1984. Topical administration of a pharmaceutical agent can result in a limited distribution of the agent to the skin and surrounding tissues or, when the agent is removed from the treatment area by the bloodstream, can result in systemic distribution of the agent. However, transdermal administration desirably results in the diffusion of an agent across the barrier of the skin resulting from topical administration or other application of a pharmaceutically acceptable formulation. The stratum corneum acts as a barrier and few pharmaceutical agents are able to penetrate intact skin. In contrast, the epidermis and dermis are permeable to many solutes and absorption of drugs therefore occurs more readily through skin that is abraded or otherwise stripped of the stratum corneum to expose the epidermis. Transdermal delivery includes injection or other delivery through any portion of the skin or mucous membrane and absorption or permeation through the remaining portion. Absorption through intact skin can be enhanced by placing the active agent in an appropriate pharmaceutically acceptable vehicle before application to the skin. Passive topical administration may consist of applying the active agent directly to the treatment site in combination with emollients or penetration enhancers.

A topically (e.g., transdermally) administrable pharmaceutical formulation may also include an amount of a form of hyaluronic acid sufficient to transport the composition through the skin of a patient into the epidermis or dermis where the composition remains until discharged via the lymphatic system. Desirably, the active compound is 1-5% by weight of the formulation and hyaluronic acid is 1-3% by weight of the formulation. Desirable forms of hyaluronic acid have a molecular weight greater than about 150,000 daltons and less than 750,000 daltons. Salts of hyaluronic acid are also desirable for use in the methods encompassed by the present invention.

Many of the compounds of the present invention can be provided as pharmaceutically acceptable acid addition salts. Such pharmaceutically acceptable acid addition salts are those salts that retain the biological effectiveness and properties of the free bases.

Parenteral Administration

The compounds described herein (e.g., compounds of Formulas (I), (I-a), (I-a-1), and (I-a-2)) for use in the methods of the invention can be administered in a pharmaceutically acceptable parenteral (e.g., intravenous or intramuscular) formulation as described herein. Additional information regarding parenteral formulations can be found, for example, in the United States Pharmacopeia-National Formulary (USP-NF), herein incorporated by reference. The parenteral formulation can be any of the five general types of preparations identified by the USP-NF as suitable for parenteral administration:

(1) "Drug Injection:" a liquid preparation that is a drug substance (e.g., a compound of Formula (I), (I-a), (I-a-1), or (I-a-2), or any of Compounds (1a)-(1n)), or a solution thereof (2) "Drug for Injection:" the drug substance (e.g., a compound of Formula (I), (I-a), (I-a-1), or (I-a-2), or any of Compounds (1a)-(1n)) as a dry solid that will be combined with the appropriate sterile vehicle for parenteral administration as a drug injection;

(3) "Drug Injectable Emulsion:" a liquid preparation of the drug substance (e.g., a compound of Formula (I), (I-a), (I-a-1), or (I-a-2), or any of Compounds (1a)-(1n)) that is dissolved or dispersed in a suitable emulsion medium;

(4) "Drug Injectable Suspension:" a liquid preparation of the drug substance (e.g., a compound of Formula (I), (I-a), (I-a-1), or (I-a-2), or any of Compounds (1a)-(1n)) suspended in a suitable liquid medium; and (5) "Drug for Injectable Suspension:" the drug substance (e.g., a compound of Formula (I), (I-a), (I-a-1), or (I-a-2), or any of Compounds (1a)-(1n)) as a dry solid that will be combined with the appropriate sterile vehicle for parenteral administration as a drug injectable suspension.

The parenteral formulation can be formulated for prompt release or for sustained/extended release of the compound. Exemplary formulations for parenteral release of the compound include: aqueous solutions, powders for reconstitution, cosolvent solutions, oil/water emulsions, suspensions, oil-based solutions, liposomes, microspheres, and polymeric gels. suspension, or as an oil-based solution.

Intramuscular Administration

The vascularity of skeletal muscles can allow small molecule or lipophilic compounds to rapidly enter the bloodstream. Accordingly, a compound of the invention (e.g., a compound of Formula (I), (I-a), (I-a-1), or (1-a-2), or any of Compounds (1a)-(1n)), or a pharmaceutical composition thereof, can be administered to a patient via intramuscular injection in, for example, the gluteal region (e.g., the ventrogluteal or the dorsogluteal muscles) or in the deltoid or vastus lateralis muscles. For example, when a compound is administered via intramuscular injection, the compound can be formulated as an aqueous solution, a powder for reconstitution, a cosolvent solution, or an emulsion. The site of intramuscular injection varies according to the age of the patient (e.g., infant or adult human) or to vary the rate of absorption of the compound (e.g., injection into the deltoid muscle will lead to faster absorption than injection into the gluteal muscles because the former is more vascular). The rate of absorption can also be influenced by the liquid carrier used in the parenteral formulation (e.g., oily formulations will be absorbed more slowly than aqueous formulations).

Synthetic Methodology

The chemistry outlined in Scheme 1 depicts a route to (+/−)-(2S,3S)-Methyl 3-acetoxy-5-(2-(dimethylamino) ethyl)-2-(4-methoxyphenyl)-4-oxo-2,3,4,5-tetrahydrobenzo[b][1,4]thiazepine-9-carboxylate (1a), a compound of the invention (e.g., a compound of Formula (I), (I-a), or (I-a-1)). The designation (+/−) used in the nomenclature presented here indicates that the described stereochemistry (in this case (2S,3S)) is racemic and the compound is a mixture of enantiomers (i.e. a 1:1 mixture of (2S,3S) and (2R,3R).

Scheme 1

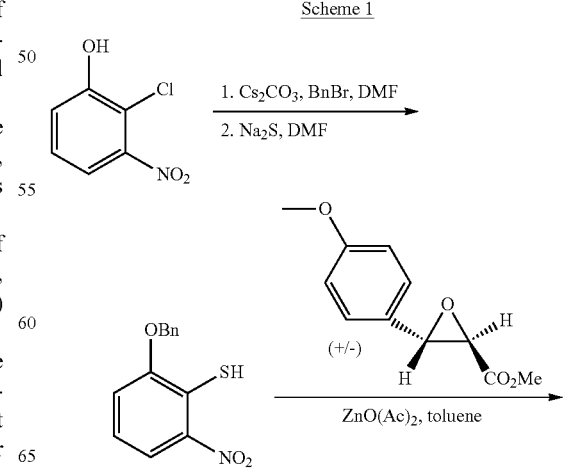

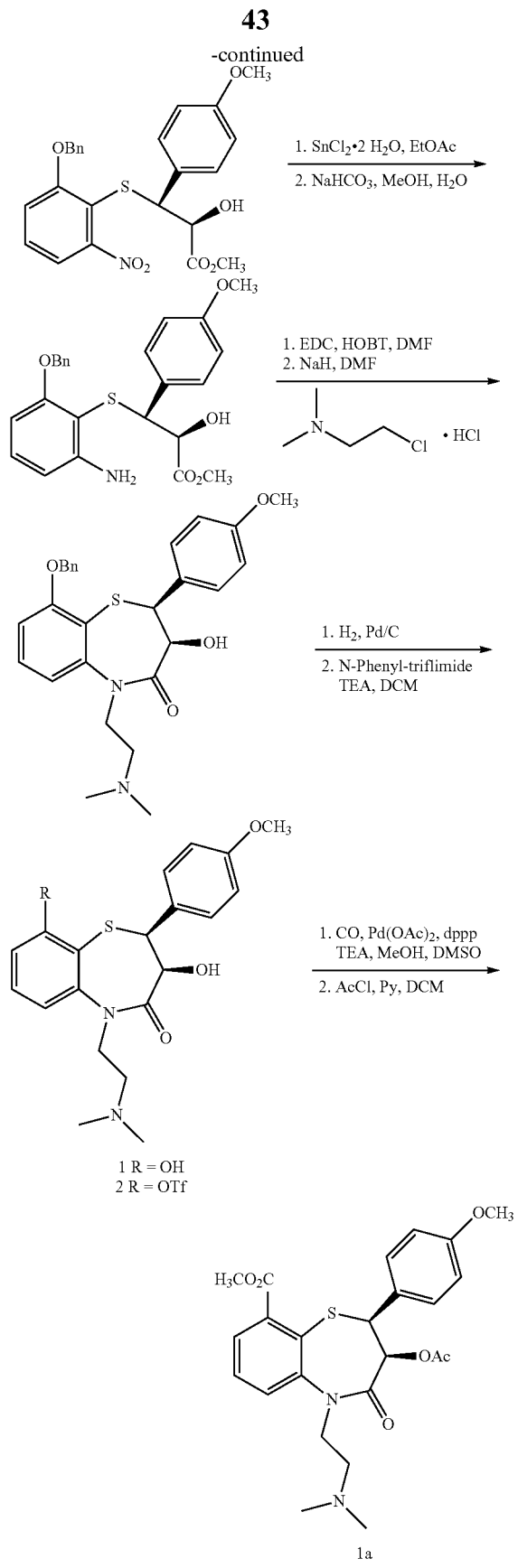

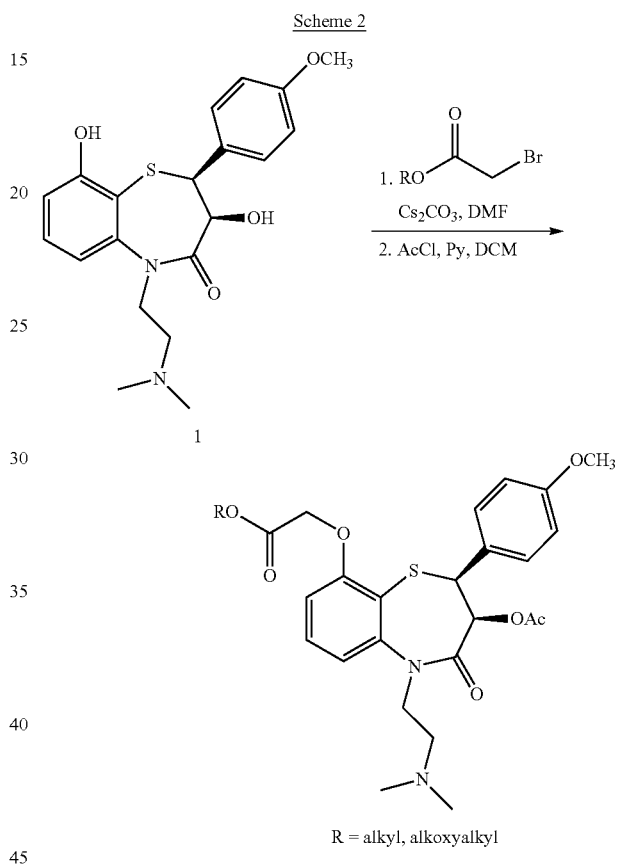

R = alkyl, alkoxyalkyl

Portions of the synthesis shown in Scheme 1 are precedented by analogy to previously described chemical transformations (Inoue et al., *J. Med. Chem.*, 34:675-687, 1991). The route may be modified to provide access to additional compounds of Formulas (I), (I-a), (I-a-1), and (I-a-2) by substituting other alcohols for methanol in the palladium mediated carbonylation of intermediate 2.

Additionally, intermediate 1 can be reacted with ester functionalized carbon electrophiles such as an alkyl or alkoxyalkyl bromoacetate followed by acetylation to give ester functionalized compounds of the invention as shown in Scheme 2.

Scheme 2

The nomenclature and abbreviations used to indicate reagents and solvents in the Schemes presented are defined as follows: benzyl bromide (BnBr); dimethylformamide (DMF); ethyl acetate (EtOAc); methanol (MeOH); 1-[3-(dimethylamino)propyl]-3-ethylcarbodiimide hydrochloride (EDC); 1-hydroxybenzotriazole (HOBT); 10% palladium on carbon (Pd/C); N-phenyltrifluoromethanesulfonimide (N-Phenyl-triflimide); triethyamine (TEA); carbon monoxide (CO); 1,3-bis(diphenylphosphino)propane (dppp); dimethylsulfoxide (DMSO); pyridine (Py); dichloromethane (DCM).

By applying the chemistry outlined in Schemes 1 and 2, other regioisomeric compounds of the invention can be prepared. For instance, substituting 2-chloro-3-nitrophenol with 3-fluoro-4-nitrophenol in Scheme 1 yields the key intermediates 3 and 4 which can be transformed to other compounds of Formulas (I), (I-a), or (I-a-1) as described.

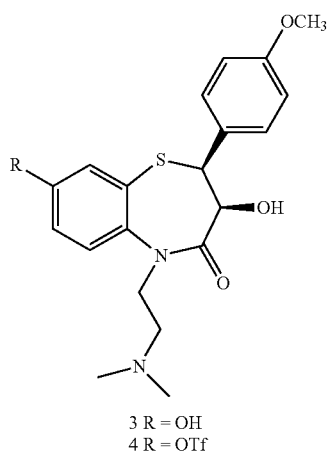

3 R = OH
4 R = OTf

Furthermore, substituting 2-chloro-3-nitrophenol with 4-fluoro-3-nitrophenol in Scheme 1 yields the key intermediates 5 and 6 which can be transformed to other compounds of Formulas (I), (I-a), (I-a-1), and (I-a-2) as described.

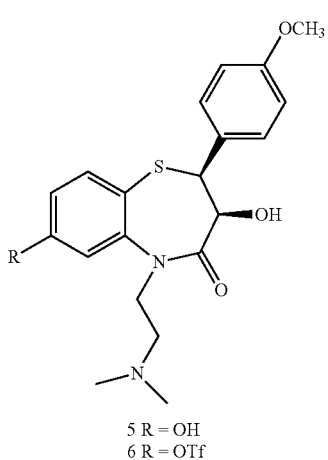

5 R = OH
6 R = OTf

Compounds of the invention (e.g., Formulas (I), (I-a), and (I-a-1)) may also be prepared by a route starting from (+)-diltiazem as shown in Scheme 3 for the synthesis of methyl 4-((2S,3S)-3-acetoxy-5-(2-(dimethylamino)ethyl)-4-oxo-2,3,4,5-tetrahydrobenzo[b][1,4]thiazepin-2-yl)benzoate.

Scheme 3

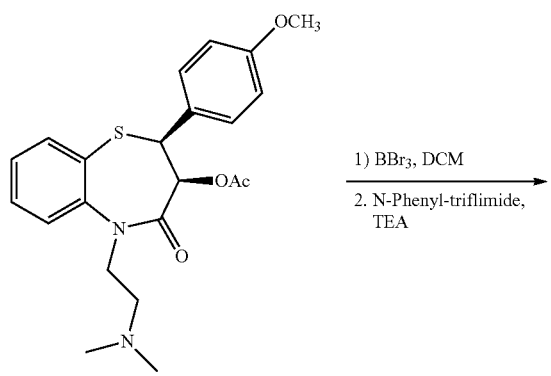

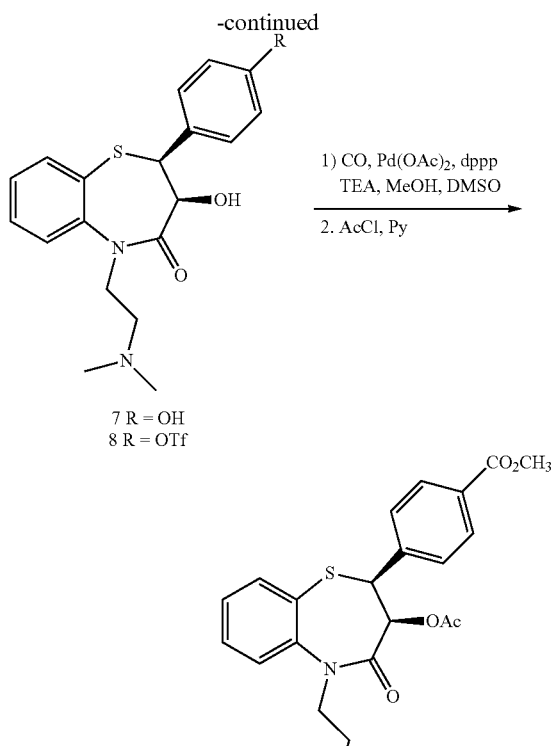

7 R = OH
8 R = OTf

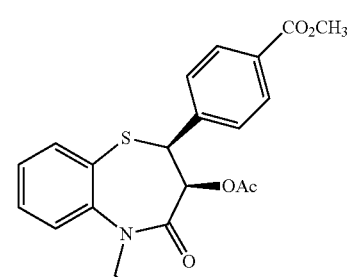

The intermediates 7 and 8 can likewise provide access to numerous compounds of Formulas (I), (I-a), or (I-a-1).

Similar chemistry can be used to access the following intermediates 9 and 10 to provide 6-substituted benzothiazepine compounds of Formulas (I) and (I-a). For each of Intermediates 2, 4, 6, 8, and 10, performing the carbonylation reaction in the presence of varying alcohols can afford access to other carboxylic ester compounds of Formulas (I), (I-a), (I-a-1), and (I-a-2).

EXAMPLES

Compounds of Formulas (I), (I-a), (I-a-1), and (I-a-2) Exemplified in this Invention The compounds of Formulas (I), (I-a), (I-a-1), and (I-a-2) exemplified in this invention are depicted in Table 1.

TABLE 1

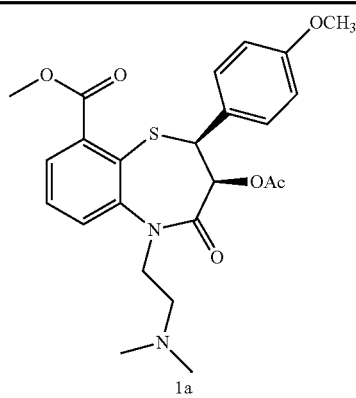

1a

TABLE 1-continued
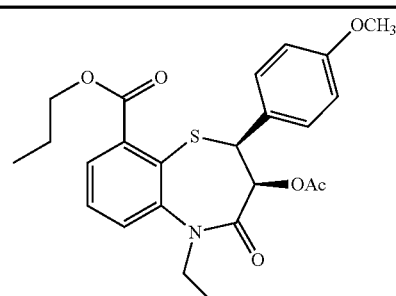
1b
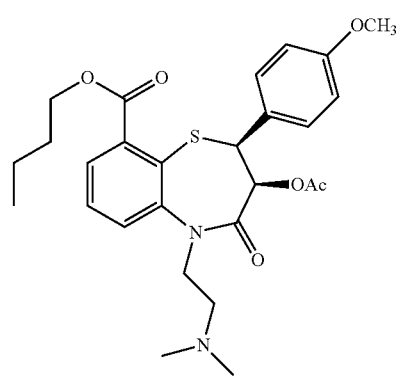 [SMILES: CCCCOC(=O)c1cccc2c1S[C@@H](c1ccc(OC)cc1)[C@@H](OC(C)=O)C(=O)N2CCN(C)C]
1c
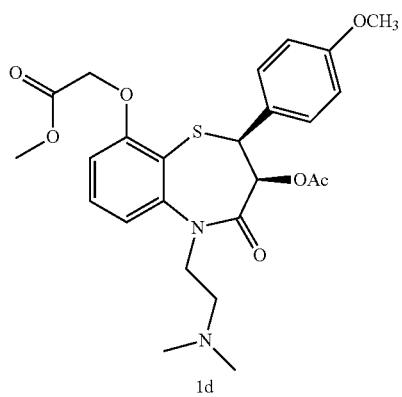
1d
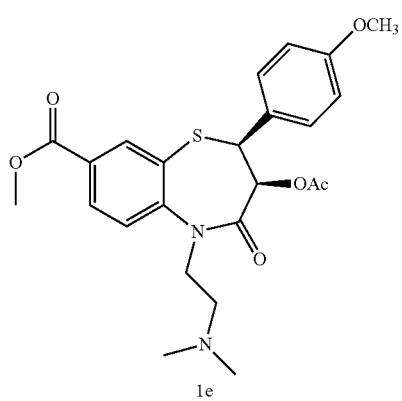
1e
TABLE 1-continued
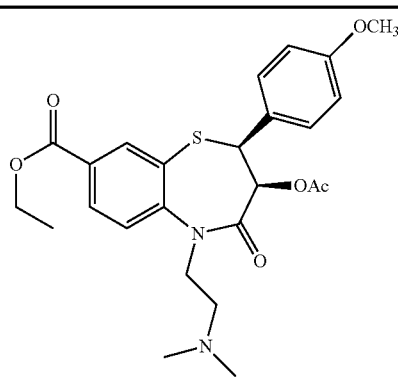
1f
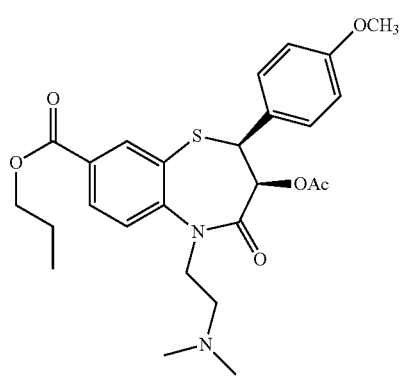
1g
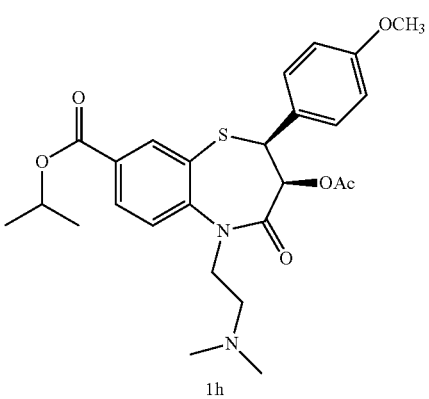
1h
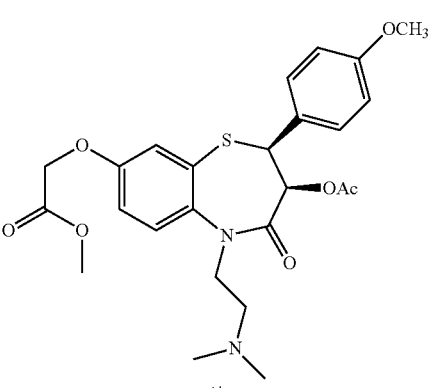
1i TABLE 1-continued

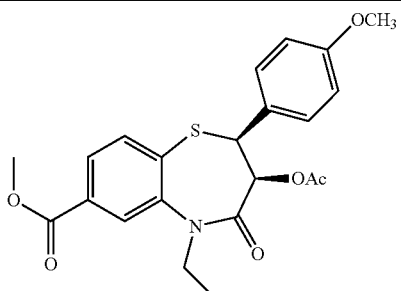
1j

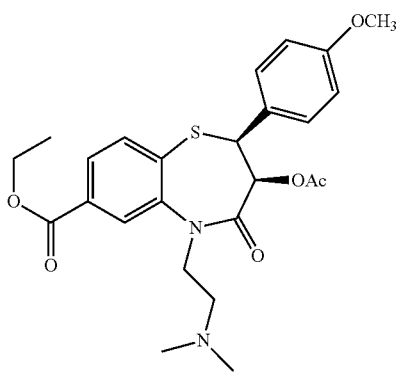
1k

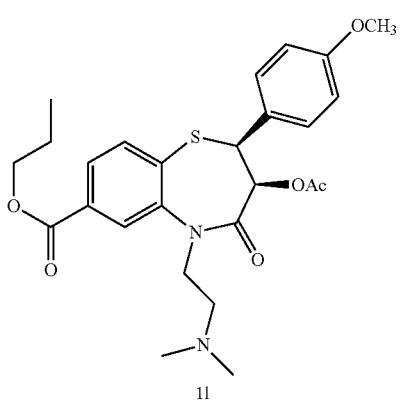
1l

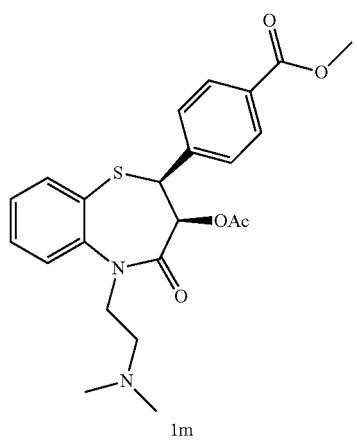
1m

TABLE 1-continued

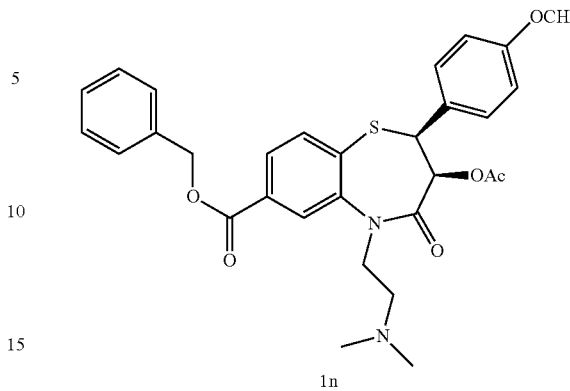
1n

The compounds of Table 1 may be alternatively described using the following nomenclature:

1a: (+/−)-(2S,3S)-Methyl 3-acetoxy-5-(2-(dimethylamino) ethyl)-2-(4-methoxyphenyl)-4-oxo-2,3,4,5-tetrahydrobenzo[b][1,4]thiazepine-9-carboxylate;

1b: (+/−)-(2S,3S)-Propyl 3-acetoxy-5-(2-(dimethylamino) ethyl)-2-(4-methoxyphenyl)-4-oxo-2,3,4,5-tetrahydrobenzo[b][1,4]thiazepine-9-carboxylate;

1c: (+/−)-(2S,3S)-Butyl 3-acetoxy-5-(2-(dimethylamino) ethyl)-2-(4-methoxyphenyl)-4-oxo-2,3,4,5-tetrahydrobenzo[b][1,4]thiazepine-9-carboxylate;

1d: (+/−)-Methyl 2-((2S,3S)-3-acetoxy-5-(2-(dimethylamino)ethyl)-2-(4-methoxyphenyl)-4-oxo-2,3,4,5-tetrahydrobenzo[b][1,4]thiazepin-9-yloxy)acetate;

1e: (+/−)-(2S,3S)-Methyl 3-acetoxy-5-(2-(dimethylamino) ethyl)-2-(4-methoxyphenyl)-4-oxo-2,3,4,5-tetrahydrobenzo[b][1,4]thiazepine-8-carboxylate;

1f: (+/'1)-(2S,3S)-Ethyl 3-acetoxy-5-(2-(dimethylamino) ethyl)-2-(4-methoxyphenyl)-4-oxo-2,3,4,5-tetrahydrobenzo[b][1,4]thiazepine-8-carboxylate;

1g: (+/−)-(2S,3S)-Propyl 3-acetoxy-5-(2-(dimethylamino) ethyl)-2-(4-methoxyphenyl)-4-oxo-2,3,4,5-tetrahydrobenzo[b][1,4]thiazepine-8-carboxylate;

1h: (+/−)-(2S,3S)-Isopropyl 3-acetoxy-5-(2-(dimethylamino)ethyl)-2-(4-methoxyphenyl)-4-oxo-2,3,4,5-tetrahydrobenzo[b][1,4]thiazepine-8-carboxylate;

1i: (+/−)-Methyl 2-((2S,3S)-3-acetoxy-5-(2-(dimethylamino)ethyl)-2-(4-methoxyphenyl)-4-oxo-2,3,4,5-tetrahydrobenzo[b][1,4]thiazepin-8-yloxy)acetate;

1j: (+/−)-(2S,3S)-Methyl 3-acetoxy-5-(2-(dimethylamino) ethyl)-2-(4-methoxyphenyl)-4-oxo-2,3,4,5-tetrahydrobenzo[b][1,4]thiazepine-7-carboxylate;

1k: (+/−)-(2S,3S)-Ethyl 3-acetoxy-5-(2-(dimethylamino) ethyl)-2-(4-methoxyphenyl)-4-oxo-2,3,4,5-tetrahydrobenzo[b][1,4]thiazepine-7-carboxylate;

1l: (+/−)-(2S,3S)-Propyl 3-acetoxy-5-(2-(dimethylamino) ethyl)-2-(4-methoxyphenyl)-4-oxo-2,3,4,5-tetrahydrobenzo[b][1,4]thiazepine-7-carboxylate;

1m: (+)-Methyl 4-((2S,3S)-3-acetoxy-5-(2-(dimethylamino) ethyl)-4-oxo-2,3,4,5-tetrahydrobenzo[b][1,4]thiazepin-2-yl)benzoate; and 1n: (+/−)-(2S,3S)-benzyl 3-acetoxy-5-(2-(dimethylamino) ethyl)-2-(4-methoxyphenyl)-4-oxo-2,3,4,5-tetrahydrobenzo[b][1,4]thiazepine-7-carboxylate.

Preparation of Compounds of Formula (I), (I-a), (I-a-1), and (I-a-2) Exemplified in this Invention In order that this invention be more fully understood, the following preparative examples are set forth. These examples are for the purpose of illustration only and are not to be construed as limiting the scope of the invention in any way.

Compounds needed as synthetic starting materials that were not available from commercial sources were synthesized. If not mentioned otherwise, all evaporations were performed under reduced pressure, preferably between about 15 mm Hg and 100 mm Hg. The structure of final products, intermediates and starting materials was confirmed by standard analytical methods such as $^1$H NMR and MS.

Example 1

1: (+/−)-(2S,3S)-5-(2-(dimethylamino)ethyl)-3,9-dihydroxy-2-(4-methoxyphenyl)-2,3-dihydrobenzo[b][1,4]thiazepin-4(5H)-one and 2: (+/−)-(2S,3S)-5-(2-(dimethylamino)ethyl)-3-hydroxy-2-(4-methoxyphenyl)-4-oxo-2,3,4,5-tetrahydrobenzo[b][1,4]thiazepin-9-yl trifluoromethanesulfonate A mixture of 5.37 g (30.9 mmol) of 2-chloro-3-nitrophenol and 12.6 g (38.7 mmol) of cesium carbonate in 60 mL of dimethylformamide (DMF) was cooled to 0° C. and 4.04 mL (34.0 mmol) of benzyl bromide was added. The mixture was warmed to 22° C. and stirred for 16 hours. Water was added and the resulting mixture was extracted with ether. The organic extract was dried (Na$_2$SO$_4$) and evaporated. The residue was crystallized from ethyl acetate and hexane to give 1-(benzyloxy)-2-chloro-3-nitrobenzene.

To a solution of 8.56 g (32.5 mmol) of 1-(benzyloxy)-2-chloro-3-nitrobenzene in 120 mL of DMF was added 15.6 g (64.9 mmol) of pulverized sodium sulfide nonahydrate. The mixture was stirred vigorously at 22° C. for 30 hours and then poured into a vigorously stirred mixture of ether and 1 N HCl. The organic layer was washed with water then brine, dried (Na$_2$SO$_4$), and evaporated. The residue was crystallized from dichloromethane (DCM) and hexane to give 2-(benzyloxy)-6-nitrobenzenethiol.

To a solution of 7.13 g (27.3 mmol) of 2-(benzyloxy)-6-nitrobenzenethiol in 100 mL of toluene was added 7.38 g (35.5 mmol) of (+/−)-methyl-trans-3-(4-methoxyphenyl)glycidate followed by 1.20 g (5.46 mmol) of zinc acetate dihydrate. The solution was stirred at 22° C. for 64 hours. Water was added, and the mixture was extracted with ethyl acetate, washed with brine, dried (Na$_2$SO$_4$), and evaporated. The compound was purified by flash chromatography on silica gel, eluting with 10% ethyl acetate/hexane gradually increasing to 35% ethyl acetate/hexane to give (+/−)-(2S,3S)-methyl 3-(2-(benzyloxy)-6-nitrophenylthio)-2-hydroxy-3-(4-methoxyphenyl)propanoate.

To 3.91 g (8.34 mmol) of (+/−)-(2S,3S)-methyl 3-(2-(benzyloxy)-6-nitrophenylthio)-2-hydroxy-3-(4-methoxyphenyl)propanoate in 45 mL of ethyl acetate was added 11.3 g (5.00 mmol) of tin(II) chloride dihydrate, and the solution was stirred at 22° C. for 3.5 hours. Water, NaHCO$_3$, and ethyl acetate were added, and the mixture was stirred at 22° C. for 1.5 hours. The stirring was stopped, and the mixture left to stand for 16 hours. The organic layer was partially separated from the aqueous layer, and the remaining mixture was filtered through Celite. The filtrate was extracted with ethyl acetate. The organic layers were combined, dried (Na$_2$SO$_4$), filtered, and evaporated to give (+/−)-(2S,3S)-methyl 3-(2-amino-6-(benzyloxy)phenylthio)-2-hydroxy-3-(4-methoxyphenyl)propanoate, which was used directly in the next step without purification.

To a solution of 2.95 g (6.71 mmol) of (+/−)-(2S,3S)-methyl 3-(2-amino-6-(benzyloxy)phenylthio)-2-hydroxy-3-(4-methoxyphenyl)propanoate in 34 mL of 9:1 methanol/water was added 5.64 g (67.1 mmol) of sodium bicarbonate. The mixture was refluxed for 16 hours, cooled to 22° C., and 500 mL of water was added. The aqueous layer was washed with ethyl acetate (2×) and then acidified to ph 4-5 with conc. HCl. The mixture was extracted 3 times with a 7:3 ethyl acetate/methanol solution. The organic layers were combined, dried (Na$_2$SO$_4$), and evaporated to give (+/−)-(2S,3S)-3-(2-amino-6-(benzyloxy)phenylthio)-2-hydroxy-3-(4-methoxyphenyl)propanoic acid.

To a solution of 2.11 g (4.96 mmol) of (+/−)-(2S,3S)-3-(2-amino-6-(benzyloxy)phenylthio)-2-hydroxy-3-(4-methoxyphenyl)propanoic acid in 25 mL of DMF was added 1.24 g (6.47 mmol) of N-(3-dimethylaminopropyl)-N'-ethylcarbodiimide hydrochloride and 871 mg (6.45 mmol) of 1-hydroxybenzotriazole. The solution was stirred at 22° C. for 16 hours, and a solution of 7:3 ethyl acetate/methanol was added to the reaction. The organic layer was washed with 1 N HCl (2×) and then with a 1:1 mixture of satd. NaHCO$_3$ and brine (2×). The organic layer was dried (Na$_2$SO$_4$) and evaporated. The residue was purified by flash chromatography on silica gel, eluting first with hexane then gradually increasing to 40% ethyl acetate/hexane to give (+/−)-(2S,3S)-9-(benzyloxy)-3-hydroxy-2-(4-methoxyphenyl)-2,3-dihydrobenzo[b][1,4]thiazepin-4(5H)-one.

To a solution of 751 mg (1.85 mmol) of (+/−)-(2S,3S)-9-(benzyloxy)-3-hydroxy-2-(4-methoxyphenyl)-2,3-dihydrobenzo[b][1,4]thiazepin-4(5H)-one in 7 mL of DMF was added 81 mg (2.03 mmol) of sodium hydride (60% dispersion in mineral oil). The mixture was stirred at 22° C. for 30 minutes. In a separate flask, 408 mg (2.03 mmol) of 2-(dimethylamino)ethylchloride hydrochloride and 81 mg (2,03 mmol) of sodium hydride (60% dispersion in mineral oil), was added to 7 mL of DMF. The mixture was stirred for 30 minutes at 22° C. and then added to the former mixture. The reaction was heated to 45° C. and stirred for 27 hours. A mixture of 1:1 saturated NaHCO$_3$ and water was added to the reaction, and the mixture was extracted with ethyl acetate (3×). The organic layers were combined, washed with brine, dried (Na$_2$SO$_4$), and evaporated. The resulting crude product was purified by flash chromatography on silica gel, eluting first with DCM then gradually increasing to 3.5% methanol/DCM to give (+/−)-(2S,3S)-9-(benzyloxy)-5-(2-(dimethylamino)ethyl)-3-hydroxy-2-(4-methoxyphenyl)-2,3-dihydrobenzo[b][1,4]thiazepin-4(5H)-one.

A solution of 653 mg (1.37 mmol) of (+/−)-(2S,3S)-9-(benzyloxy)-5-(2-(dimethylamino)ethyl)-3-hydroxy-2-(4-methoxyphenyl)-2,3-dihydrobenzo[b][1,4]thiazepin-4(5H)-one in 25 mL of methanol was flushed with nitrogen and 300 mg of 10% Pd/C was added. The reaction was flushed with H$_2$ and stirred for 18 hours at 22° C. under a balloon/H$_2$ atmosphere. The mixture was filtered through Celite, and the filtrate was evaporated. The residue was crystallized from ethyl acetate/hexane to give 1. MS found M+H=389.

To a solution of 308 mg (0.794 mmol) of 1 in 10 mL of DCM was added 283 mg (0.794 mmol) of N-phenyltrifluoromethanesulfonimide and 330 µL (2.38 mmol) of triethylamine. The solution was stirred at 22° C. for 22 hours, and the reaction was then partitioned between 1 M NaOH and DCM. The organic layer was washed with water, dried ($Na_2SO_4$), and evaporated to give 2. MS found M+H=521.

Example 2

1a: (+/−)-(2S,3S)-Methyl 3-acetoxy-5-(2-(dimethylamino)ethyl)-2-(4-methoxyphenyl)-4-oxo-2,3,4,5-tetrahydrobenzo[b][1,4]thiazepine-9-carboxylate To a solution of 81 mg (0.155 mmol) of 2 in 2 mL of methanol was added 9 mg (0.039 mmol) of palladium(II) acetate, 16 mg (0.039 mmol) of 1,3-bis(diphenylphosphino)propane, 66 µL (0.093 mmol) of dimethylsulfoxide, and 130 µL (0.093 mmol) of triethylamine. The mixture was stirred at 50° C. under a balloon/carbon monoxide atmosphere for 16 hours. DCM was added, and the organic layer was washed with saturated $NaHCO_3$, dried ($Na_2SO_4$), and evaporated. The residue was purified by flash chromatography on silica gel, eluting with DCM then gradually increasing to 3% methanol/DCM to give (+/−)-(2S,3S)-methyl 5-(2-(dimethylamino)ethyl)-3-hydroxy-2-(4-methoxyphenyl)-4-oxo-2,3,4,5-tetrahydrobenzo[b][1,4]thiazepine-9-carboxylate.

To a solution of 19 mg (0.045 mmol) of (+/−)-(2S,3S)-methyl 5-(2-(dimethylamino)ethyl)-3-hydroxy-2-(4-methoxyphenyl)-4-oxo-2,3,4,5-tetrahydrobenzo[b][1,4]thiazepine-9-carboxylate in 0.5 mL of DCM was added 22 µL (0.27 mmol) of pyridine and 4 µL (0.06 mmol) of acetyl chloride. The reaction was stirred at 22° C. for 3 hours. The reaction mixture was diluted with DCM, washed sequentially with 1 M $Na_2CO_3$ and water, dried ($Na_2SO_4$), and evaporated. The residue was purified by flash chromatography on silica gel, eluting with DCM then gradually increasing to 3% methanol/DCM to give 1a. MS found M+H=473. The hydrochloride salt of 1a was recrystallized from ethyl acetate; mp 169-172° C.

Example 3

1b: (+/−)-(2S,3S)-Propyl 3-acetoxy-5-(2-(dimethylamino)ethyl)-2-(4-methoxyphenyl)-4-oxo-2,3,4,5-tetrahydrobenzo[b][1,4]thiazepine-9-carboxylate Transformation of 2 to 1b was accomplished in a manner analogous to that described in Example 2 by substituting 1-propanol for methanol in the palladium mediated carbonylation reaction. MS found M+H=501. The oxalate salt of 1b was recrystallized from ethyl acetate; mp 107-109° C.

Example 4

1c: (+/−)-(2S,3S)-Butyl 3-acetoxy-5-(2-(dimethylamino)ethyl)-2-(4-methoxyphenyl)-4-oxo-2,3,4,5-tetrahydrobenzo[b][1,4]thiazepine-9-carboxylate Transformation of 2 to 1c was accomplished in a manner analogous to that described in Example 2 by substituting 1-butanol for methanol in the palladium mediated carbonylation reaction. MS found M+H=515. The oxalate salt of 1c was recrystallized from ethyl acetate; mp 183-186° C.

Example 5

1d: (+/−)-Methyl 2-((2S,3S)-3-acetoxy-5-(2-(dimethylamino)ethyl)-2-(4-methoxyphenyl)-4-oxo-2,3,4,5-tetrahydrobenzo[b][1,4]thiazepin-9-yloxy)acetate A mixture of 83 mg (0.214 mmol) of 1 and 105 mg (0.321 mmol) of cesium carbonate in 4 mL of DMF was stirred at 22° C. for 5 minutes, and 214 µL (0.214 mmol) of methyl bromoacetate (1 M in dioxane) was added. The reaction was stirred at 22° C. for 2 hours then partitioned between ethyl acetate and water. The organic layer was washed with brine (2×), dried ($Na_2SO_4$), and evaporated to give (+/−)-methyl 2-((2S,3S)-5-(2-(dimethylamino)ethyl)-3-hydroxy-2-(4-methoxyphenyl)-4-oxo-2,3,4,5-tetrahydrobenzo[b][1,4]thiazepin-9-yloxy)acetate as an oil. The product was transformed to 1d by an acetylation procedure analogous to that described in Example 2. MS found M+H=503. The oxalate salt of 1d was recrystallized from ethyl acetate; mp 152-160° C.

Example 6

3: (+/−)-(2S,3S)-5-(2-(dimethylamino)ethyl)-3,8-dihydroxy-2-(4-methoxyphenyl)-2,3-dihydrobenzo[b][1,4]thiazepin-4(5H)-one and 4: (+/−)-(2S,3S)-5-(2-(dimethylamino)ethyl)-3-hydroxy-2-(4-methoxyphenyl)-4-oxo-2,3,4,5-tetrahydrobenzo[b][1,4]thiazepin-8-yl trifluoromethanesulfonate The preparation of 3 and 4 was accomplished in a manner analogous to 1 and 2 by substituting 3-fluoro-4-nitrophenol for 2-chloro-3-nitrophenol and conducting the sequence of reactions described in Example 1. MS found for 3 M+H=389. MS found for 4 M+H=521.

Example 7

1e: (+/−)-(2S,3S)-Methyl 3-acetoxy-5-(2-(dimethylamino)ethyl)-2-(4-methoxyphenyl)-4-oxo-2,3,4,5-tetrahydrobenzo[b][1,4]thiazepine-8-carboxylate Transformation of 4 to 1e was accomplished in a manner analogous to that described in Example 2 by substituting 4 for 2 in the palladium mediated carbonylation reaction. MS found M+H=473. The oxalate salt of 1e was recrystallized from ethyl acetate; mp 185-194° C.

Example 8

1f: (+/−)-(2S,3S)-Ethyl 3-acetoxy-5-(2-(dimethylamino)ethyl)-2-(4-methoxyphenyl)-4-oxo-2,3,4,5-tetrahydrobenzo[b][1,4]thiazepine-8-carboxylate Transformation of 4 to 1f was accomplished in a manner analogous to that described in Example 2 by substituting ethanol for methanol and 4 for 2 in the palladium mediated carbonylation reaction. MS found M+H=487. The oxalate salt of 1f was recrystallized from ethyl acetate; mp 167-171° C.

Example 9

1g: (+/−)-(2S,3S)-Propyl 3-acetoxy-5-(2-(dimethylamino)ethyl)-2-(4-methoxyphenyl)-4-oxo-2,3,4,5-tetrahydrobenzo[b][1,4]thiazepine-8-carboxylate Transformation of 4 to 1 g was accomplished in a manner analogous to that described in Example 2 by substituting 1-propanol for methanol and 4 for 2 in the palladium mediated carbonylation reaction. MS found M+H=501. The oxalate salt of 1g was recrystallized from ethyl acetate; mp 114-119° C.

Example 10

1h: (+/−)-(2S,3S)-Isopropyl 3-acetoxy-5-(2-(dimethylamino)ethyl)-2-(4-methoxyphenyl)-4-oxo-2,3,4,5-tetrahydrobenzo[b][1,4]thiazepine-8-carboxylate Transformation of 4 to 1h was accomplished in a manner analogous to that described in Example 2 by substituting 2-propanol for methanol and 4 for 2 in the palladium mediated carbonylation reaction. MS found M+H=501. The oxalate salt of 1h was recrystallized from ethyl acetate; mp 190-193° C.

Example 11

(+/−)-Methyl 2-((2S,3S)-3-acetoxy-5-(2-(dimethylamino)ethyl)-2-(4-methoxyphenyl)-4-oxo-2,3,4,5-tetrahydrobenzo[b][1,4]thiazepin-8-yloxy)acetate Transformation of 3 to 1i was performed in a manner analogous to that described in Example 5 by substituting 3 for 1. Subsequent acetylation as described afforded 1i. MS found M+H=503. The oxalate salt of 1i was recrystallized from ethyl acetate; mp 174-175° C.

Example 12

5: (+/−)-(2S,3S)-5-(2-(dimethylamino)ethyl)-3,7-dihydroxy-2-(4-methoxyphenyl)-2,3-dihydrobenzo[1,4]thiazepin-4(5H)-one and 6: (+/−)-(2S,3S)-5-(2-(dimethylamino)ethyl)-3-hydroxy-2-(4-methoxyphenyl)-4-oxo-2,3,4,5-tetrahydrobenzo[b][1,4]thiazepin-7-yl trifluoromethanesulfonate The preparation of 5 and 6 was accomplished in a manner analogous to 1 and 2 by substituting 4-fluoro-3-nitrophenol for 2-chloro-3-nitrophenol and conducting the sequence of reactions described in Example 1. MS found for 5 M+H=389. MS found for 6 M+H=521.

Example 13

1j: (+/−)-(2S,3S)-Methyl 3-acetoxy-5-(2-(dimethylamino)ethyl)-2-(4-methoxyphenyl)-4-oxo-2,3,4,5-tetrahydrobenzo[b][1,4]thiazepine-7-carboxylate Transformation of 6 to 1j was accomplished in a manner analogous to that described in Example 2 by substituting 6 for 2 in the palladium mediated carbonylation reaction. MS found M+H=473. A partial oxalate salt of 1j was prepared by mixing 1.0 molar equivalents of 1j with 0.6 molar equivalents of oxalic acid in a solution of DCM and methanol, evaporating, and then triturating the residue with ether.

Example 14

1k: (+/−)-(2S,3S)-Ethyl 3-acetoxy-5-(2-(dimethylamino)ethyl)-2-(4-methoxyphenyl)-4-oxo-2,3,4,5-tetrahydrobenzo[b][1,4]thiazepine-7-carboxylate Transformation of 6 to 1k was accomplished in a manner analogous to that described in Example 2 by substituting ethanol for methanol and 6 for 2 in the palladium mediated carbonylation reaction. MS found M+H=487. A partial oxalate salt of 1k was prepared by mixing 1.0 molar equivalents of 1k with 0.6 molar equivalents of oxalic acid in a solution of DCM and methanol, evaporating, and then triturating the residue with ether.

Example 15

1l: (+/−)-(2S,3S)-Propyl 3-acetoxy-5-(2-(dimethylamino)ethyl)-2-(4-methoxyphenyl)-4-oxo-2,3,4,5-tetrahydrobenzo[b][1,4]thiazepine-7-carboxylate Transformation of 6 to 1l was accomplished in a manner analogous to that described in Example 2 by substituting 1-propanol for methanol and 6 for 2 in the palladium mediated carbonylation reaction. MS found M+H=501. A partial oxalate salt of 1l was prepared by mixing 1.0 molar equivalents of 1l with 0.6 molar equivalents of oxalic acid in a solution of DCM and methanol, evaporating, and then triturating the residue with ether.

Example 16

1m: (+)-Methyl 4-((2S,3S)-3-acetoxy-5-(2-(dimethylamino)ethyl)-4-oxo-2,3,4,5-tetrahydrobenzo[b][1,4]thiazepin-2-yl)benzoate To 1.00 g (2.22 mmol) of (+)-diltiazem hydrochoride in 22 mL of DCM at −78° C. was slowly added 629 μL (6.66 mmol) of boron tribromide. The solution was stirred for 16 hours at 22° C., and an additional 629 μL (6.66 mmol) of boron tribromide was added slowly. The solution was stirred for another 2 hours at 22° C. The reaction was then cooled to 0° C., and about 10 mL of water was added carefully. The mixture was partitioned between DCM and saturated NaHCO$_3$. The aqueous layer was extracted with DCM (3×), and the combined organic layers were dried (Na$_2$SO$_4$), filtered, and evaporated to give (2S,3S)-5-(2-(dimethylamino)ethyl)-3-hydroxy-2-(4-hydroxyphenyl)-2,3-dihydrobenzo[b][1,4]thiazepin-4(5H)-one. The compound was used without further purification.

To 228 mg (0.636 mmol) of (2S,3S)-5-(2-(dimethylamino)ethyl)-3-hydroxy-2-(4-hydroxyphenyl)-2,3-dihydrobenzo[b][1,4]thiazepin-4(5H)-one in 3 mL of DCM was added 178 μL (1.28 mmol) of triethylamine followed by 296 mg (0.829 mmol) N-phenyltrifluoromethanesulfonimide. The solution was stirred at 22° C. for 16 hours and then evaporated. The residue was purified by flash chromatography on silica gel, eluting first with DCM and then gradually increasing to 7% methanol/DCM to give 4-((2S,3S)-5-(2-(dimethylamino)

ethyl)-3-hydroxy-4-oxo-2,3,4,5-tetrahydrobenzo[b][1,4]thiazepin-2-yl)phenyl trifluoromethanesulfonate.

To a solution of 156 mg (0.318 mmol) of 4-((2S,3S)-5-(2-(dimethylamino)ethyl)-3-hydroxy-4-oxo-2,3,4,5-tetrahydrobenzo[b][1,4]thiazepin-2-yl)phenyl trifluoromethanesulfonate in 0.50 mL of methanol was added 0.23 mL of dimethyl sulfoxide (3.2 mmol), 0.28 mL (2.0 mmol) of triethylamine, 49.9 mg (0.222 mmol) of palladium(II)acetate, and 65.5 mg (0.159 mmol) of 1,3-bis(diphenylphosphino)propane. The mixture was stirred under a balloon/carbon monoxide atmosphere for 16 hours at 50° C. then cooled to 22° C. The solvent was evaporated and then co-evaporated with xylene (2×). The residue was purified by flash chromatography on silica gel, eluting first with DCM then gradually increasing to 5% methanol/DCM to give methyl 4-((2S,3S)-5-(2-(dimethylamino)ethyl)-3-hydroxy-4-oxo-2,3,4,5-tetrahydrobenzo[b][1,4]thiazepin-2-yl)benzoate.

To 127 mg (0.317 mmol) of methyl 4-((2S,3S)-5-(2-(dimethylamino)ethyl)-3-hydroxy-4-oxo-2,3,4,5-tetrahydrobenzo[b][1,4]thiazepin-2-yl)benzoate in 160 µL of pyridine at 0° C. was added 25 µL (0.35 mmol) of acetyl chloride. The solution was stirred at 0° C. for 2 hours. The solvent was evaporated to leave a residue which was co-evaporated with toluene (3×). The material was then dissolved in DCM, washed with 1 N NaOH, dried ($Na_2SO_4$), and evaporated. Purification was afforded by flash chromatography on silica gel, eluting first with DCM then gradually increasing to 5% methanol/DCM to give 1m. MS found M+H=443. The observed $^1$H NMR coupling constants between the $C_2$ and $C_3$ methine protons (J=7.4 Hz) confirmed retention of the cis stereochemical relationship. The hydrochloride salt of 1m was recrystallized from isopropanol/ether; mp 214-216° C.; $[\alpha]^{25}_D$+98.9° (c 0.99, $CHCl_3$).

Example 17

1n: (+/−)-(2S,3S)-benzyl 3-acetoxy-5-(2-(dimethylamino)ethyl)-2-(4-methoxyphenyl)-4-oxo-2,3,4,5-tetrahydrobenzo[b][1,4]thiazepine-7-carboxylate Transformation of 6 to 1n was accomplished in a manner analogous to that described in Example 2 by substituting benzyl alcohol for methanol and 6 for 2 in the palladium mediated carbonylation reaction. MS found M+H=549. The oxalate salt of 1n was prepared and triturated with a mixture of ethyl acetate and ether to give a partially crystalline solid.

Example 18

Calcium Channel Binding Data

Calcium channel binding inhibition constants ($K_i$) were determined as follows.

Whole brains of male Wistar derived rats weighing 175±25 grams were used to prepare L-type benzothiazepine calcium channel in modified Tris-HCl buffer (pH 7.4). A 0.5 mg aliquot was incubated with 2 nM [$^3$H]Diltiazem (PerkinElmer NET-847) for 180 minutes at 4° C. Non-specific binding was estimated in the presence of 10 µM diltiazem (RBI D-112). Membranes were filtered and washed, the filters were then counted to determine [$^3$H]Diltiazem specifically bound. All determinations were performed in duplicate. Specific binding was determined as the difference of total and nonspecific binding. The $K_i$ values were calculated using the equation of Cheng and Prusoff (Cheng et al., *Biochem. Pharmacol.* 22:3099-3018,1973) using the observed $IC_{50}$ of the tested compound, the concentration of the radioligand employed in the assay, and the historical values for the $K_d$ of the ligand (obtained experimentally at MDS Pharma Services).

The same method was used to determine the $K_i$ for diltiazem-HCl and 1m-HCl (Table 3).

TABLE 3

| Compound # | Structure | $K_i$ (µM) Ca Channel |
|---|---|---|
| 1m•HCl | 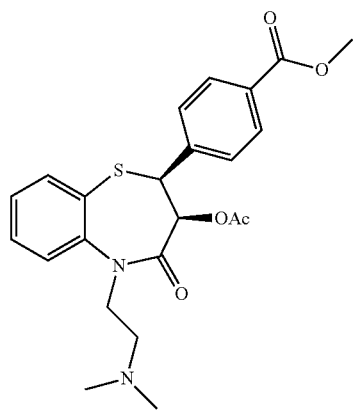 | ++ |

TABLE 3-continued

| Compound # | Structure | $K_i$ (μM) Ca Channel |
|---|---|---|
| Diltiazem•HCl | [structure of diltiazem hydrochloride] | ++++ |
| 1a•HCl | [structure with methyl ester at 9-position] •HCl | +++ |
| 1j•oxalic acid | [structure with methyl ester at 7-position] •(CO$_2$H)$_2$ | ++++ |
| 1d•oxalic acid | [structure with methoxycarbonylmethoxy group] •(CO$_2$H)$_2$ | + |

TABLE 3-continued

| Compound # | Structure | $K_i$ (μM) Ca Channel |
|---|---|---|
| 1b•oxalic acid | 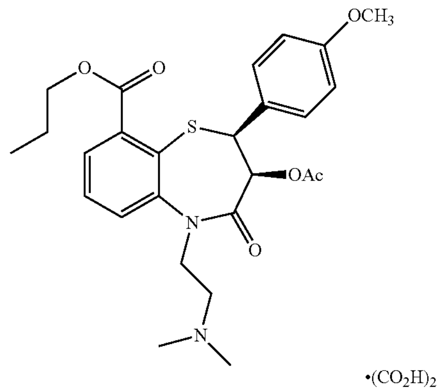 | +++ |
| 1e•oxalic acid | 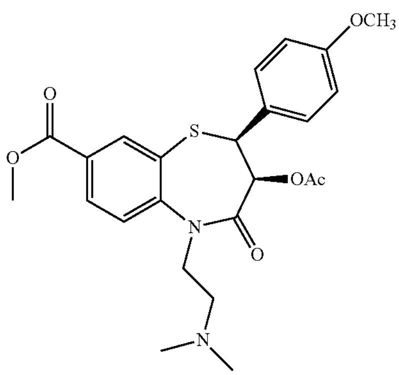 [SMILES: COC(=O)c1ccc2c(c1)S[C@@H](c1ccc(OC)cc1)[C@@H](OC(C)=O)C(=O)N2CCN(C)C] | +++ |
| 1f•oxalic acid | 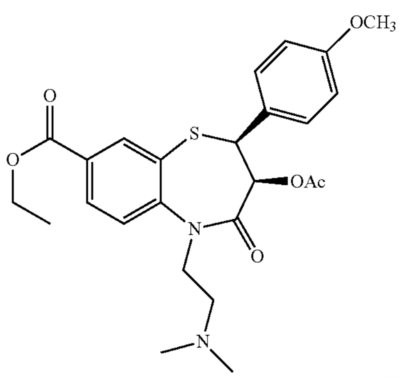 [SMILES: CCOC(=O)c1ccc2c(c1)S[C@@H](c1ccc(OC)cc1)[C@@H](OC(C)=O)C(=O)N2CCN(C)C] | +++ |
| 1i•oxalic acid | 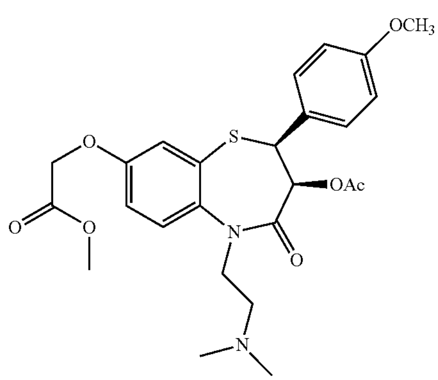 [SMILES: COC(=O)COc1ccc2c(c1)S[C@@H](c1ccc(OC)cc1)[C@@H](OC(C)=O)C(=O)N2CCN(C)C] | + |

TABLE 3-continued
| Compound # | Structure | $K_i$ (μM) Ca Channel |
|---|---|---|
| 1h•oxalic acid | 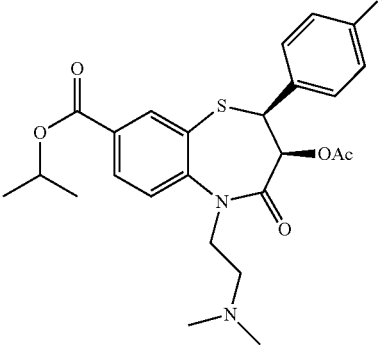 •(CO$_2$H)$_2$ | +++ |
| 1k•oxalic acid | 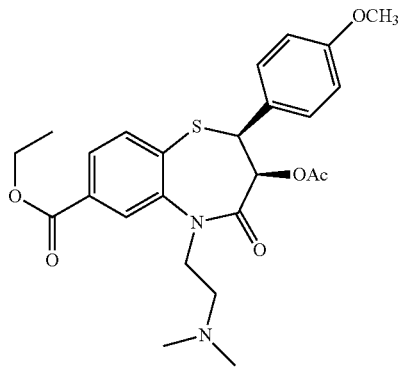 [SMILES: CCOC(=O)c1ccc2c(c1)N(CCN(C)C)C(=O)[C@H](OC(C)=O)[C@H](c1ccc(OC)cc1)S2] •(CO$_2$H)$_2$ | ++++ |
| 1g•oxalic acid | 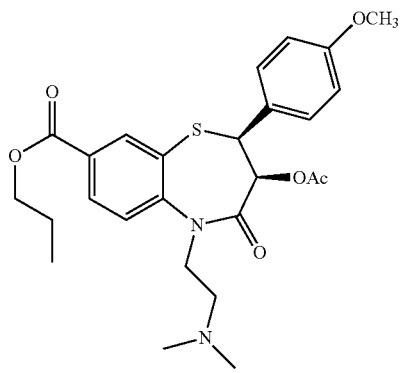 •(CO$_2$H)$_2$ | +++ |
| 1c•oxalic acid | 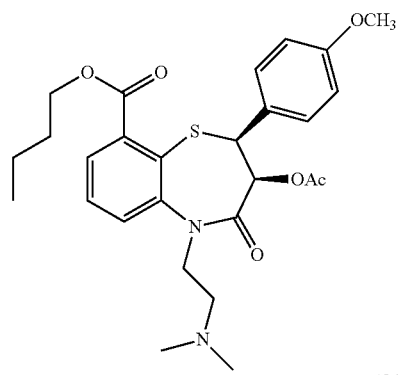 •(CO$_2$H)$_2$ | +++ |

TABLE 3-continued

| Compound # | Structure | $K_i$ (μM) Ca Channel |
|---|---|---|
| 1l•oxalic acid | 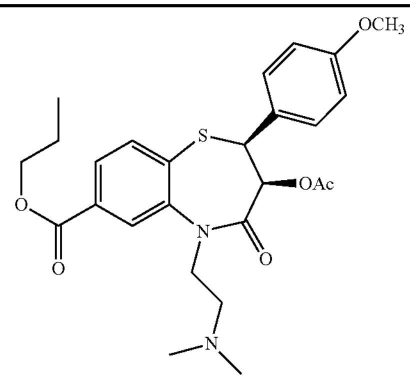 | ++++ |
| 1n•oxalic acid | 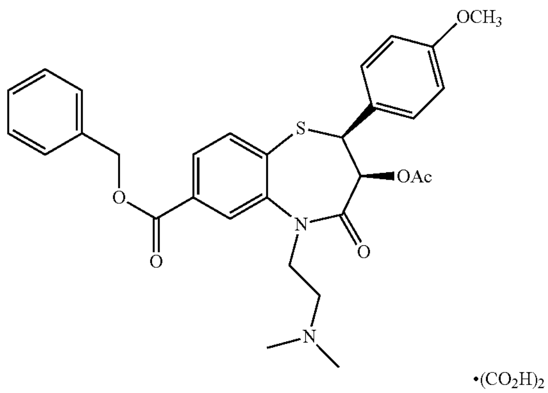 [SMILES: COc1ccc([C@@H]2Sc3ccc(C(=O)OCc4ccccc4)cc3N(CCN(C)C)C(=O)[C@@H]2OC(C)=O)cc1 ; "·(CO2H)2"] | +++ |

Table Legend:
+ = $K_i$ is greater than 1.0 μM
++ = $K_i$ is 0.5-1.0 μM
+++ = $K_i$ is 0.1-0.5 μM
++++ = $K_i$ is less than 0.1 μM Method for Assaying Stability in Human Plasma The sensitivity of the CCB analogs to hydrolysis by esterase enzymes can be inferred by measuring their stability in human plasma. This measure provides a qualitative in-vitro method of ranking the compounds in order of relative stability and provides a useful comparison to CCBs with longer half-lives (e.g., diltiazem, verapamil, and nifedipine). Such assays are available from commercial service providers such as MDS Pharma Services. The assay is conducted in the following manner:

The test matrix is pooled human plasma;
The concentration of the analog being tested is 10 μM;
The mixture is incubated in duplicate at 37° C.;
The incubation is stopped at 0, 0.5, 1, 2, and 30 minutes by adding an equal volume of acetonitrile; and
The extracted samples are analyzed by either (+)- or (−)-ESI LC/MS using a pre-established generic method.
Data is expressed as % of the zero time samples.

OTHER EMBODIMENTS

While the invention has been described in connection with specific embodiments thereof, it will be understood that it is capable of further modifications and this application is intended to cover any variations, uses, or adaptations of the invention following, in general, the principles of the invention and including such departures from the present disclosure come within known or customary practice within the art to which the invention pertains and may be applied to the essential features hereinbefore set forth.

All references, patents, patent application publications, and patent applications, including U.S. Provisional Application No. 61/189,747, filed Aug. 22, 2008, cited herein are hereby incorporated by reference to the same extent as if each of these references, patents, patent application publications, and patent applications were separately incorporated by reference herein.

What is claimed is:

1. A pharmaceutical composition comprising a compound having a structure according the following formula

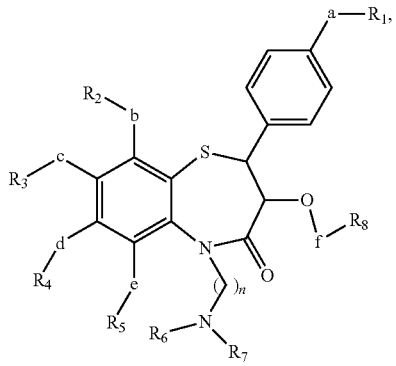

or a pharmaceutically acceptable addition salt thereof, wherein each linker a, b, c, d, and e is, independently, $CH_2$, O, S, or a single bond;

linker f is C(O) or a single bond;

each $R_1$, $R_2$, $R_3$, $R_4$, and $R_5$ is, independently, H, F, Cl, Br, substituted or unsubstituted lower alkyl, substituted or unsubstituted lower alkoxyalkyl, or $CO_2R_9$;

each $R_6$ and $R_7$ is, independently, H, substituted or unsubstituted lower alkyl, or substituted or unsubstituted lower alkoxyalkyl;

$R_8$ is H, substituted or unsubstituted lower alkyl, substituted or unsubstituted aryl, or substituted or unsubstituted lower alkoxyalkyl;

$R_9$ is substituted or unsubstituted lower alkyl, substituted or unsubstituted lower alkoxyalkyl, substituted or unsubstituted aryl, substituted or unsubstituted heteroaryl, substituted or unsubstituted aralkyl, or substituted or unsubstituted heteroaralkyl;

n is 2, 3, or 4, where any combination of 0, 1, or 2 methyl or ethyl groups in total can be substituted on any of the methylene groups in the chain; and wherein when any $R_1$, $R_2$, $R_3$, $R_4$, or $R_5$ is H, F, Cl, or Br, the corresponding linker is a single bond; and at least one of a-$R_1$, b-$R_2$, c-$R_3$, d-$R_4$, or e-$R_5$ is (single bond)-$CO_2R_9$ or at least one of a-$R_1$, b-$R_2$, c-$R_3$, d-$R_4$, or e-$R_5$ is O-(lower alkyl substituted with $CO_2R_9$), or at least one of a-$R_1$, b-$R_2$, c-$R_3$, d-$R_4$, or e-$R_5$ is O-(lower alkoxyalkyl substituted with $CO_2R_9$).

2. The pharmaceutical composition of claim 1, wherein n is 2.

3. The pharmaceutical composition of claim 1, wherein said compound has the following structure

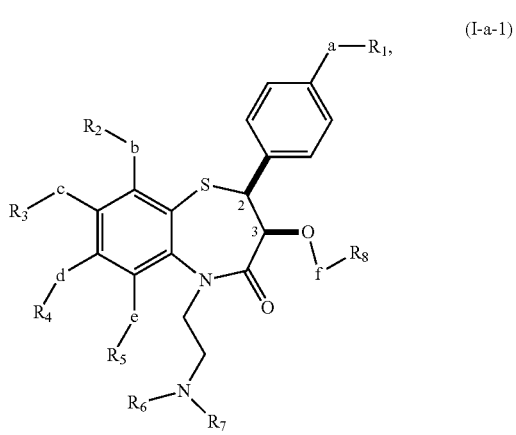

wherein a, b, c, d, e, f, $R_1$, $R_2$, $R_3$, $R_4$, $R_5$, $R_6$, $R_7$, $R_8$, and $R_9$ are as defined for the formula of claim 1 and wherein the $C_6H_4$-a-$R_1$ group at C2 and the O-f-$R_8$ group at C3 are cis to one another.

4. The pharmaceutical composition of claim 3, wherein said compound has the following structure

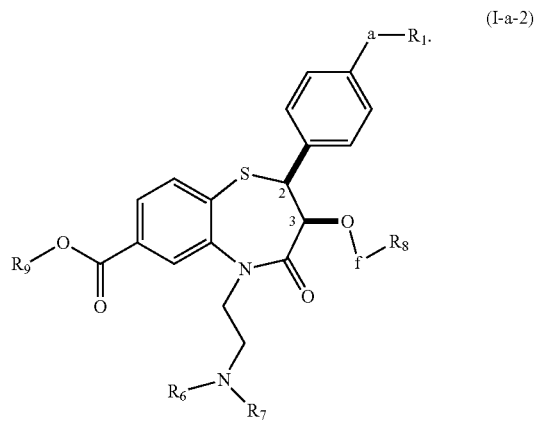

5. The pharmaceutical composition of claim 3, wherein carbons C2 and C3 each have the S-configuration.

6. The pharmaceutical composition of claim 3, wherein said compound is selected from the group consisting of:

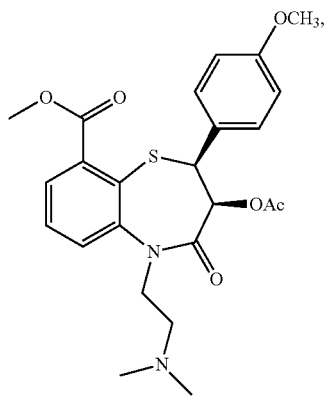

69
-continued
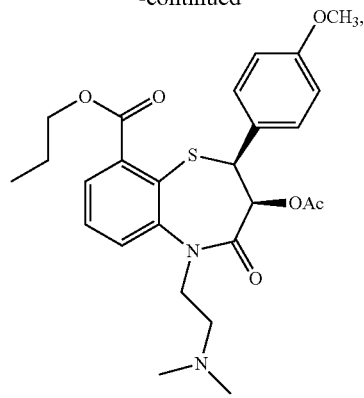
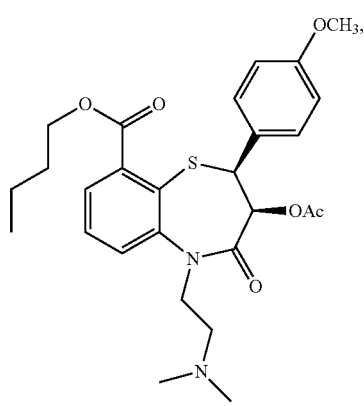
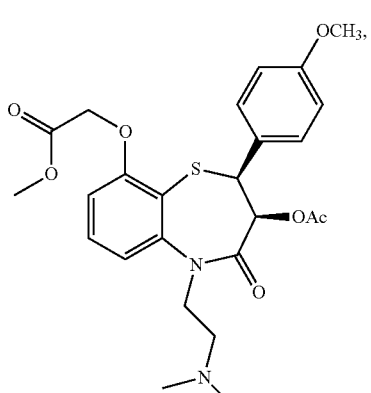
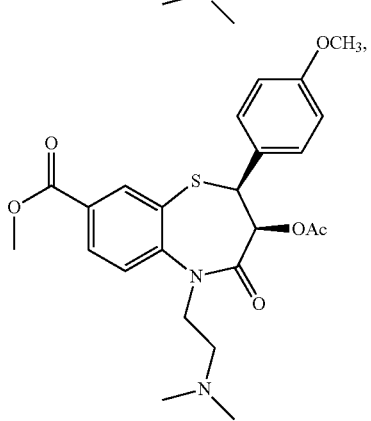
70
-continued
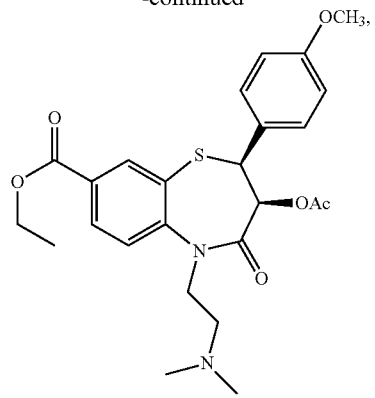
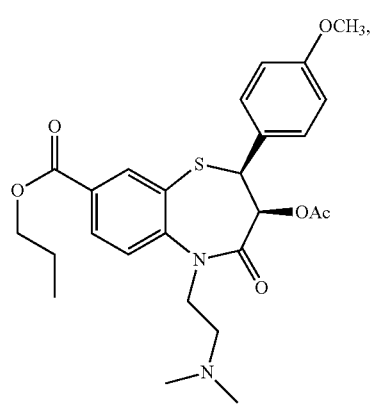
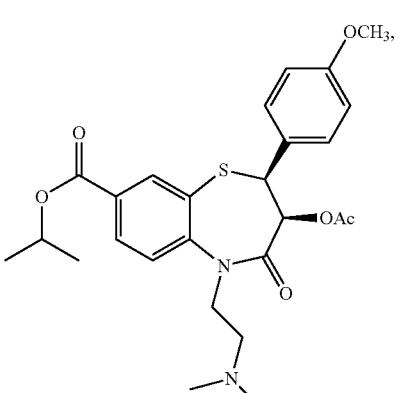
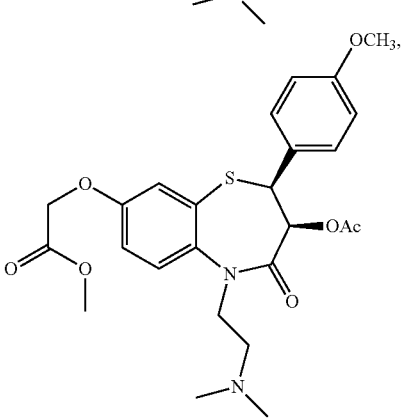

71
-continued
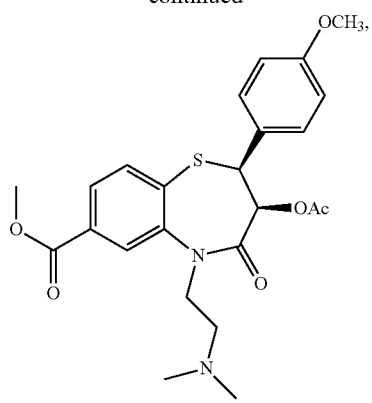
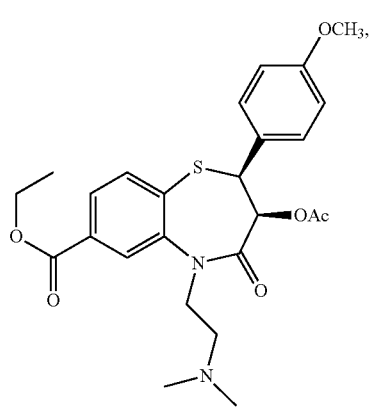
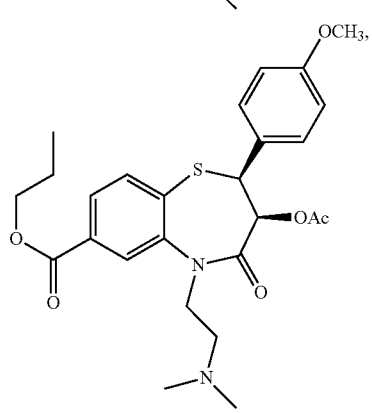
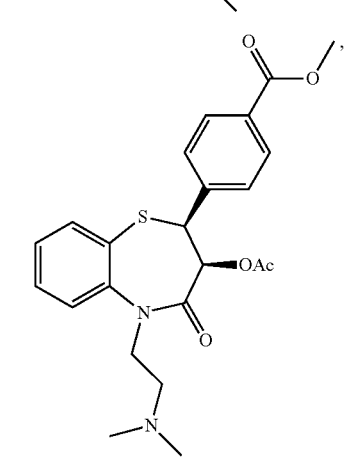
72
-continued
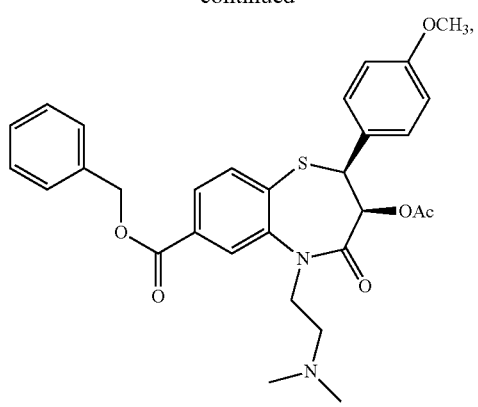
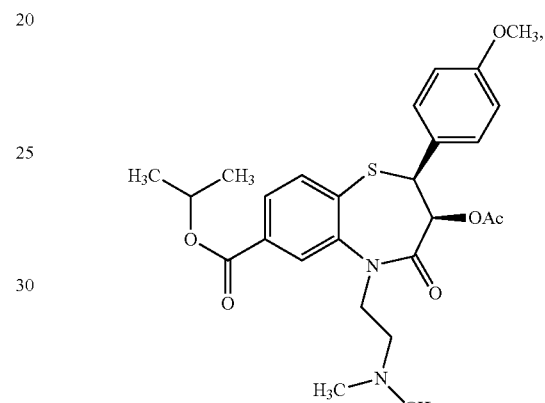
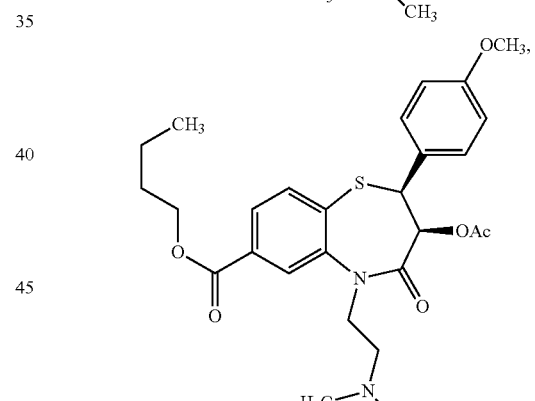
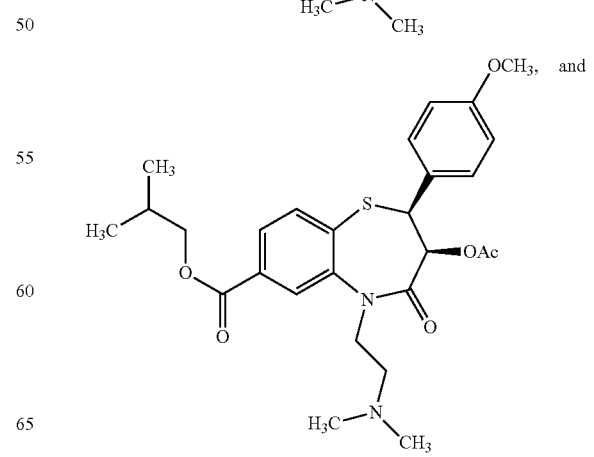

-continued

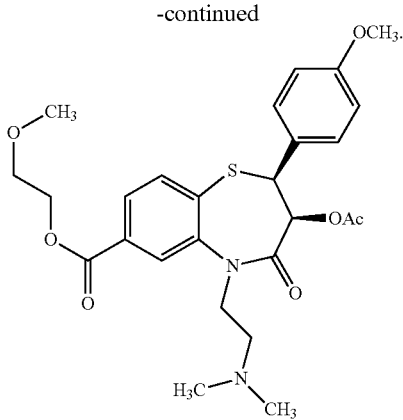

7. The pharmaceutical composition of claim 1, wherein one of a-$R_1$, b-$R_2$, c-$R_3$, d-$R_4$, or e-$R_5$ is (single bond)-$CO_2R_9$.

8. The pharmaceutical composition of claim 1, wherein $R_9$ is substituted or unsubstituted lower alkyl.

9. The pharmaceutical composition of claim 1, wherein $R_9$ is substituted or unsubstituted lower alkoxyalkyl.

10. The pharmaceutical composition of claim 1, wherein a-$R_1$ is O-(unsubstituted lower alkyl) or O-(substituted lower alkyl).

11. The pharmaceutical composition of claim 1, wherein a-$R_1$ is (single bond)-$CO_2R_9$.

12. The pharmaceutical composition of claim 1, wherein $R_6$ and $R_7$ are both substituted or unsubstituted lower alkyl.

13. The pharmaceutical composition of claim 1, wherein f-$R_8$ is C(O)-(unsubstituted lower alkyl) or C(O)-(substituted lower alkyl).

14. The pharmaceutical composition of claim 1, wherein e-$R_5$ is (single bond)-H.

15. The pharmaceutical composition of claim 1, wherein said composition comprises the hydrochloric acid addition salt of said compound.

16. The pharmaceutical composition of claim 1, wherein said composition is formulated for parenteral administration.

17. The pharmaceutical composition of claim 16, wherein said administration is intramuscular.

18. The pharmaceutical composition of claim 1, wherein
at least one of a-$R_1$, b-$R_2$, c-$R_3$, d-$R_4$, or e-$R_5$ is (single bond)-$CO_2R_9$, or
at least one of a-$R_1$, b-$R_2$, c-$R_3$, d-$R_4$, or e-$R_5$ is O-(lower alkyl substituted with $CO_2R_9$).

19. A method of treating an ischemic heart condition or cardiac arrhythmia, said method comprising administering to a patient in need thereof a therapeutically effective amount of a compound having a structure according to claim 18.

20. The method of claim 19, wherein said administering comprises sublingual, buccal, transdermal, intranasal, inhalation, or intramuscular administration.

21. A method of treating a hypertensive crisis in an emergency room setting, said method comprising administering to a patient in need thereof a therapeutically effective amount of a compound having a structure according to claim 18.

22. The method of claim 21, wherein said administering comprises sublingual, buccal, intranasal, inhalation, or parenteral administration.

23. A method of treating hypertension before, during or after surgery, or no-reflow phenomenon following reperfusion, said method comprising administering to a patient in need thereof a therapeutically effective amount of a compound having a structure according to claim 18.

24. The method of claim 23, wherein said administering comprises parenteral administration.

25. A method of treating hypertension, wherein said method comprises administering to a patient in need thereof a therapeutically effective amount of a compound having a structure according to claim 18.

26. The method of claim 25, wherein said administering comprises parenteral administration.

27. A method of treating a disease associated with decreased skeletal muscle blood flow, wherein said disease is Raynaud's phenomenon or intermittent claudication, said method comprising administering to a patient in need thereof a therapeutically effective amount of a compound having a structure according to claim 18.

28. The method of claim 27, wherein said administering comprises sublingual, buccal, transdermal, intranasal, inhalation, topical, or parenteral administration.

* * * * *